US006342509B1

United States Patent
Hirschfeld et al.

(10) Patent No.: US 6,342,509 B1
(45) Date of Patent: *Jan. 29, 2002

(54) PIPERIDINE QUATERNARY SALTS- CCR- 3 RECEPTOR ANTAGONISTS

(75) Inventors: Donald Roy Hirschfeld; Denis John Kertesz, both of Mountain View; David Berard Smith, San Mateo, all of CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/442,799

(22) Filed: Nov. 18, 1999

Related U.S. Application Data
(60) Provisional application No. 60/109,293, filed on Nov. 20, 1998.

(51) Int. Cl.⁷ .................... A61K 31/445; C07D 211/68
(52) U.S. Cl. .................. 514/317; 514/316; 514/318; 514/321; 514/324; 514/326; 514/330; 546/233; 546/234; 546/235; 546/237
(58) Field of Search .................. 514/316, 317, 514/318, 321, 324, 326, 330; 566/233, 234, 235, 247

(56) References Cited

U.S. PATENT DOCUMENTS

| | | | |
|---|---|---|---|
| 4,559,349 A | 12/1985 | Storni | 514/318 |
| 4,579,947 A | 4/1986 | Devlin et al. | 544/400 |
| 4,857,330 A | 8/1989 | Stephens et al. | 424/424 |
| 5,026,858 A * | 6/1991 | Vega-noverola et al. | 546/224 |
| 5,081,246 A | 1/1992 | Hidaka et al. | 544/363 |
| 5,118,684 A | 6/1992 | Sugimoto et al. | 514/249 |
| 5,143,923 A | 9/1992 | Hrib et al. | 514/321 |
| 5,317,020 A | 5/1994 | Emonds-Alt et al. | 514/255 |
| 5,364,864 A | 11/1994 | Bigg et al. | 514/318 |
| 5,438,064 A * | 8/1995 | Mobilio et al. | 514/313 |
| 5,541,201 A | 7/1996 | Carr et al. | 514/330 |
| 5,674,881 A | 10/1997 | Emonds-Alt et al. | 514/329 |
| 5,773,620 A | 6/1998 | Emonds-Alt et al. | 546/234 |
| 5,849,732 A | 12/1998 | Suzuki et al. | 514/212 |
| 5,889,026 A | 3/1999 | Alanine | 514/326 |
| 6,090,824 A | 7/2000 | Bernstein et al. | 514/317 |
| 6,136,827 A | 10/2000 | Caldwell et al. | 514/329 |
| 6,166,015 A | 12/2000 | Rogers et al. | 514/243 |

FOREIGN PATENT DOCUMENTS

| | | | |
|---|---|---|---|
| AU | 9671774 A | 5/1997 | |
| EP | 0 661 266 A1 | 7/1995 | |
| EP | 0 673 927 A1 | 9/1995 | |
| EP | 0 802 196 A1 | 10/1997 | |
| EP | 0903349 | 3/1999 | ........ C07D/295/12 |
| EP | 0 903 349 A2 | 3/1999 | |
| JP | 4001 128 A | 1/1992 | |
| WO | WO 94/27991 | 12/1994 | |
| WO | 9710207 | 9/1995 | ........ C07D/207/04 |
| WO | WO 96/06095 | 2/1996 | |
| WO | WO 97/10207 | 3/1997 | |
| WO | 97/19060 | 5/1997 | ........ C07D/211/58 |
| WO | WO 98/04554 A1 | 2/1998 | |
| WO | WO 99/37617 | 7/1999 | |
| WO | 99/37617 | 7/1999 | ........ C07D/211/52 |
| WO | 99/37619 | 7/1999 | ........ C07D/221/16 |
| WO | WO 99/37619 | 7/1999 | |
| WO | 0035449 | 6/2000 | ........ A61K/31/445 |

OTHER PUBLICATIONS

Boyfield, I., et al., "Design and Synthesis of 2–Naphthoate Esters as Selective Dopamine D4 Antagonists", *American Chemical Society*, pp. 1946–1948, (1996).

Heath, H., et al., "Chemokine Receptor Usage by Human Eosinophils, The Importance of CCR3 Demonstrated Using an Antagonistic Monoclonal Antibody", *The American Society for Clinical Investigation*, 99 (2), pp. 178–184, (Jan. 1997).

Itoh, K., et al., "Synthesis and pharmacological evaluation of carboxamide derivatives as selective serotoninergic 5–HT4 receptor agonists", *Eur. J. Med. Chem.*, 34, pp. 329–341, (1999).

Saxena, M., et al., "Synthesis. Biological Evaluation, and Quantitative Structure–Activity Relationship Analysis of (B– (Aroylamino)ethyl)piperazines and –piperidines and (2– ((Arylamino)carbon)ethyl)piperazines, —piperidines, pyrazinpyridoindoles, and –pyrazinoisoquinolines.", *American Chemical Society*, pp. 2970–2976, (1990).

Weng, J.H., et al., "Structure–activity relationships and receptor binding characteristics of 3–methylfentanyl derivatives", *Yaoxue Xuebao*, 23 (3), Abstract, 3 pages, (1990).

U.S. patent application Ser. No. 09/441,919, Filing date Nov. 17, 1999, *4–Aroylpiperidine Derivatives– CCR–3 Receptor Antagonists*, Gong, et al. (Assignee Syntex (U.S.A.) Inc.), Docket No. R0054B–REG.

U.S. patent application Ser. No. 09/134,013, Filing date Aug. 14, 1998, *Cyclic Amine Derivatives CCR–3 Receptor Antagonists*, Gong, et al. (Assignee Syntex (U.S.A.) Inc); Docket No. R0029B–REG.

(List continued on next page.)

Primary Examiner—Ceila Chang
(74) Attorney, Agent, or Firm—Rohan Peries

(57) ABSTRACT

This invention relates to certain piperidine quatemrwy salts of Formula (I):

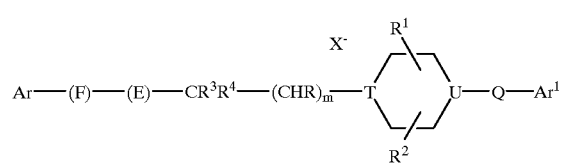

that are CCR-3 receptor antagonists, pharmaceutical compositions containing them, methods for their use and methods for preparing these compounds.

23 Claims, No Drawings

OTHER PUBLICATIONS

U.S. patent application Ser. No. 09/197,282, Filing date Nov. 20, 1998; *Cyclic Amine Derivatives CCR–3 Receptor Antagonists*, Gong, et al. (Assignee Syntex (U.S.A.) Inc); Docket No. R0029C–CIP.

Boyfield, et al., *Journal of Medicinal Chemistry*, vol. 39:10, (1996), pp 1946–1948, "Design and Aynthesis of 2–Naphthoate Esters as Selective Dopamine $D_4$ Antagonists".

Shey, et al., *Bioorganic & Medicinal Chemistry Letters*, vol. 9:4, (1999), pp 519–522, "Liquid Phase Combinatorial Synthesis of Benzylpiperazines".

Itoh, et al., *European Journal of Medicinal Chemistry*, vol. 34, (1999), pp 329–341, "Synthesis and pharmacological evaluation of carboxamide derivatives as selective serotoninergic 5–$HT_4$ receptor agonists".

Archibald et al. "Antihypertensive N–4–pieridylbenzamide derivatives" CA 79:136989, 1973.*

Weng et al. "Structure–activity relationships and receptor . . . " CA 113:70701, 1990.*

Ko et al. "Preparation of N–ureidoalkyl piperidines . . . " CA 133:43441, 2000.*

* cited by examiner

PIPERIDINE QUATERNARY SALTS- CCR- 3 RECEPTOR ANTAGONISTS

CROSS REFERENCE TO RELATED APPLICATIONS

This application claims the benefit under 35 U.S.C. 119(e) of U.S. Provisional Application Ser. No. 60/109,293, filed Nov. 20, 1998, hereby incorporated by reference in its entirety.

FIELD OF THE INVENTION

This invention relates to certain piperidine quaternary salts that are CCR-3 receptor antagonists, pharmaceutical compositions containing them, methods for their use and methods for preparing these compounds.

BACKGROUND INFORMATION

Tissue eosinophilia is a feature of a number of pathological conditions such as asthma, rhinitis, eczema and parasitic infections ((see Bousquet, J. et al. *N. Eng. J. Med.* 323: 1033–1039 (1990) and Kay, A. B. and Corrigan. C. J. *Br. Med. Bull.* 48:51–64 (1992)). In asthma, eosinophil accumulation and activation are associated with damage to bronchial epithelium and hyperresponsiveness to constrictor mediators. Chemokines such as RANTES, eotaxin and MCP-3 are known to activate eosinophils ((see Baggiolini, M. and Dahinden, C. A. *Immunol. Today.* 15:127–133 (1994), Rot, A. M. et al. *J. Exp. Med.* 176, 1489–1495 (1992) and Ponath. P. D. et al. *J. Clin. Invest.*, Vol. 97, #3, 604–612 (1996)). However, unlike RANTES and MCP-3 which also induce the migration of other leukocyte cell types, eotaxin is selectively chemotactic for eosinophils ((see Griffith-Johnson, D. A et al. *Biochem. Biophy. Res. Commun.* 197:1167 (1993) and Jose, P. J. et al. *Biochem. Biophy. Res. Commun.* 207, 788 (1994)). Specific eosinophil accumulation was observed at the site of administration of eotaxin whether by intradennal or intraperitoneal injection or aerosol inhalation ((see Griffith-Johnson, D. A et al. *Biochem. Biophy. Res. Commun.* 197:1167 (1993); Jose, P. J. et al. *J. Exp. Med.* 179, 881–887 (1994); Rothenberg, M. E. et al. *J. Exp. Med.* 181, 1211 (1995) and Ponath. P. D. *J. Clin. Invest.*, Vol. 97, #3, 604–612 (1996)).

Glucocorticoids such as dexamethasone, methprednisolone and hydrocortisone have been used for treating many eosinophil-related disorders, including bronchial asthma ((R. P. Schleimer et. al., *Am. Rev. Respir. Dis.*, 141, 559 (1990)). The glucocorticoids are believed to inhibit IL-5, IL3 mediated eosinophil survival in these diseases. However, prolonged use of glucocorticoids can lead to side effects such as glaucoma, osteoporosis and growth retardation in the patients ((see Hanania N. A et al., *J. Allergy and Clin. Immunol.*, Vol. 96, 571–579 (1995) and Saha M. T. et al, *Acta Paediatrica*, Vol. 86, #2, 138–142 (1997)). It is therefore desirable to have an alternative means of treating eosinophil related diseases without incurring these undesirable side effects.

Recently, the CCR-3 receptor was identified as a major chemokine receptor that eosinophils use for their response to eotaxin, RANTES and MCP-3. When transfected into a murine pre-β lymphoma line, CCR-3 bound eotaxin, RANTES and MCP-3 and conferred chemotactic responses on these cells to eotaxin, RANTES and MCP-3 ((see Ponath. P. D. et al. *J. Exp. Med.* 183, 2437–2448 (1996)). The CCR-3 receptor is expressed on the surface of eosinophils, T-cells (subtype Th-2), basophils and mast cells and is highly selective for eotaxin.

Studies have shown that pretreatment of eosinophils with an anti-CCR-3 mAb completely inhibits eosinophil chemotaxis to eotaxin, RANTES and MCP-3 ((see Heath H. et al. *J. Clin. Invest.*, Vol. 99, #2, 178–184 (1997)). Applicants' U.S. patent application Ser. No. 09/134,013, filed Aug. 14, 1998 discloses compounds that are CCR-3 antagonists and inhibit eosinophilic recruitment by chemokines such as eotaxin. PCT Application WO 98/04554 discloses piperidine analogs that are CCR-3 receptor antagonists.

Therefore, blocking the ability of the CCR-3 receptor to bind RANTES, MCP-3 and eotaxin and thereby preventing the recruitment of eosinophils should provide for the treatment of eosinophil-mediated inflammatory diseases.

The present invention concerns novel piperidine quaternary salts which are capable of inhibiting the binding of eotaxin to the CCR-3 receptor and thereby provide a means of combating eosinophil induced diseases, such as asthma.

SUMMARY OF THE INVENTION

In a first aspect, this invention provides compounds selected from the group of compounds represented by Formula (I):

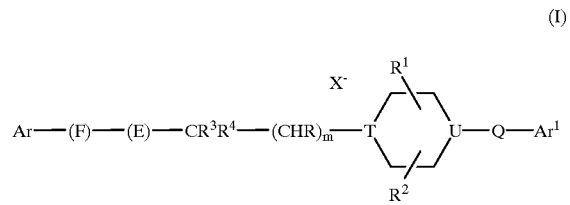

(I)

wherein:
One of T and U is —$N^+R^5$— where $R^5$ is alkyl, haloalkyl, cyanoalkyl, hydroxyalkyl, alkoxyalkyl, carboxyalkyl, alkoxycarbonylalkyl, amidoalkyl, sulfonylaminoalkyl, or aralkyl and the other is —CH—;

$X^-$ is a pharmaceutically acceptable counterion;

$R^1$ and $R^2$ are, independently of each other, hydrogen or alkyl;

m is an integer from 0 to 3 provided that when T is —$N^+R^5$— then m is at least 1;

Ar and $Ar^1$ are, independently of each other, aryl or heteroaryl;

F is alkylene, alkenylene, or a bond;

R is hydrogen or alkyl; or R together with either $R^3$ or $R^4$ and the atoms to which they are attached forms a carbocycle or a heterocycle;

$R^3$ and $R^4$ are, independently of each other, hydrogen, alkyl, alkenyl, haloalkyl, cycloalkyl, cycloalkylalkyl, aryl, aralkyl, heteroaryl, heteroaralkyl, heterocyclyl, heterocyclylalkyl, heteroalkyl, or -(alkylene)-C(O)—Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy;

E is —C(O)N($R^6$)—, —$SO_2$N($R^6$)—, —N($R^7$)C(O)N($R^6$)—, —N($R^7$)$SO_2$N($R^6$)—, —N($R^7$)C(S)N($R^6$)—, —N($R^7$)C(O)— or —N($R^7$)$SO_2$— where:
$R^6$ and $R^7$ are, independently of each other, hydrogen, alkyl, acyl, haloalkyl, cycloalkyl, cycloalkylalkyl, aryl, aralkyl, aralkenyl, heteroaryl, heteroaralkyl, heterocycloalkyl, heteroalkyl, or -(alkylene)-C(O)—Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy;

Q is —CO— or an alkylene chain optionally interrupted by —C(O)—, —NR$^8$—, —O—, —S(O)$_{0-2}$—, —C(O)N(R$^8$)—, —N(R$^8$)C(O)—, —N(R$^8$)SO$_2$—, —SO$_2$N(R$^8$)—, —N(R$^9$)C(O)N(R$^{10}$)—, —N(R$^9$)SO$_2$N(R$^{10}$)— or —N(R$^9$)C(S)N(R$^{10}$)— where:

R$^8$, R$^9$ and R$^{10}$ are, independently of each other, hydrogen, alkyl, acyl, haloalkyl, cycloalkyl, cycloalkylalkyl, aryl, aralkyl, aralkenyl, heteroaryl, heteroaralkyl, heterocyclylalkyl, heteroalkyl, or -(alkylene)-C(O)—Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy; and prodrugs, individual isomers, mixtures of isomers, and pharmaceutically acceptable salts thereof.

In a second aspect, this invention provides pharmaceutical compositions containing a therapeutically effective amount of a compound of Formula (I) or its pharmaceutically acceptable salt and a pharmaceutically acceptable excipient.

In a third aspect, this invention provides a method of treatment of a disease in a mammal treatable by administration of a CCR-3 receptor antagonist, comprising administration of a therapeutically effective amount of a compound of Formula (I) or its pharmaceutically acceptable salt. The disease states include respiratory diseases such as asthma.

In a fourth aspect, this invention provide a process for preparing compounds of Formula (I).

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, pentyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkenylene" means a linear divalent hydrocarbon radical of two to six carbon atoms or a branched divalent hydrocarbon radical of three to six carbon atoms, containing at least one double bond, e.g., ethenylene, 2,4-pentadienylene, and the like.

"Acyl" means a radical —C(O)R where R is alkyl, alkenyl, cycloalkyl, heteroalkyl, haloalkyl, aryl, aralkyl, heteroaralkyl or heteroaryl, e.g., acetyl, benzoyl, thenoyl, and the like.

"Acyloxy" means a radical —OC(O)R where R is hydrogen, alkyl, cycloalkyl, heteroalkyl, haloalkyl or optionally substituted phenyl, e.g., acetoxy, benzoyloxy, and the like.

"Acylarnino" means a radical —NRC(O)R' where R is hydrogen or alkyl and R' is alkyl, cycloalkyl, heteroalkyl, haloalkyl or optionally substituted phenyl, e.g., acetylamino, trifluoroacetylamino, benzoylamino, methylacetylamino, and the like.

"Halo" means fluoro, chloro, bromo or iodo, preferably fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Cycloalkyl" means a saturated monovalent cyclic hydrocarbon radical of three to six ring carbons, e.g., cyclopropyl, cyclohexyl, and the like.

"Carbocycle" means a saturated, cyclic group of 3 to 6 ring atoms in which all the ring atoms are carbon, e.g., cyclopentyl, cyclohexyl, and the like.

"Monosubstituted-amino" means a radical —NHR where R is alkyl, heteroalkyl, haloalkyl, cycloalkyl, cycloalkylalkyl or optionally substituted phenyl, e.g., methylamino, (1-methylethyl)amino, phenylamino, and the like.

"Disubstituted-amino" means a radical —NRR' where R and R' are independently alkyl, alkenyl, heteroalkyl, haloalkyl, cycloalkyl, cycloalkylalkyl or optionally substituted phenyl. Representative examples include, but are not limited to, dimethylamino, methylethylamino, di(1-methylethyl)amino, and the like.

"Aryl" means a monovalent monocyclic or bicyclic aromatic hydrocarbon radical of 6 to 10 ring atoms, and optionally substituted independently with one or more substituents, preferably one, two or three substituents selected from alkyl, haloalkyl, heteroalkyl, cycloalkyl, cycloalkylalkyl, halo, cyano, nitro, acyloxy, alkoxy, optionally substituted phenyl, heteroaryl, heteroaralkyl, amino, monosubstituted amino, disubstituted amino, acylamino, hydroxylarnino, amidino, guanidino, cyanoguanidinyl, hydrazino, hydrazido, —OR [where R is hydrogen, haloalkyl, alkenyl, cycloalkyl, cycloalkylalkyl, optionally substituted phenyl, heteroaryl or heteroaralkyl], —S(O)$_n$R [where n is an integer from 0 to 2 and R is hydrogen, alkyl, haloalkyl, cycloalkyl, cycloalkylalkyl, optionally substituted phenyl, heteroaryl, heteroaralkyl, amino, mono- or disubstituted amino], —NRSO$_2$R' (where R is hydrogen or alkyl and R' is alkyl, amino, mono- or disubstituted amino), —C(O)R (where R is hydrogen, alkyl, cycloalkyl, heteroalkyl, haloalkyl or optionally substituted phenyl), —COOR (where R is hydrogen, alkyl, optionally substituted phenyl, heteroaryl or heteroaralkyl), -(alkylene)COOR (where R is hydrogen, alkyl, optionally substituted phenyl, heteroaryl or heteroaralkyl), methylenedioxy, 1,2-ethylenedioxy, —CONR'R" or -(alkylene)CONR'R" (where R' and R" are independently selected from hydrogen, alkyl, cycloalkyl, haloalkyl, cycloalkylalkyl, optionally substituted phenyl, heteroaryl and heteroaralkyl). More specifically the term aryl includes, but is not limited to, phenyl, 1-naphthyl, 2-naphthyl, and derivatives thereof.

"Optionally substituted phenyl" means a phenyl group which is optionally substituted independently with one, two or three substituents selected from alkyl, haloalkyl, halo, nitro, cyano, —OR (where R is hydrogen or alkyl), —NRR' (where R and R' are independently of each other hydrogen or alkyl), —COOR (where R is hydrogen or alkyl) or —CONR'R" (where R' and R" are independently selected from hydrogen or alkyl).

"Heteroaryl" means a monovalent monocyclic or bicyclic aromatic radical of 5 to 10 ring atoms containing one, two, or three ring heteroatoms selected from N, O, or S, the remaining ring atoms being C. The aromatic radical is optionally substituted independently with one or more substituents, preferably one or two substituents selected from alkyl, haloalkyl, heteroalkyl, cycloalkyl, cycloalkylalkyl, halo, cyano, nitro, acyloxy, optionally substituted phenyl, amino, mono- or disubstituted amino, acylamino, hydroxyamino, amidino, guanidino, cyanoguanidinyl, hydrazino, hydrazido, —OR [where R is hydrogen, alkyl, haloalkyl, cycloalkyl, cycloalkylalkyl or optionally substituted phenyl], —S(O),R [where n is an integer from 0 to 2 and R is hydrogen, alkyl, haloalkyl, cycloalkyl, cycloalkylalkyl, optionally substituted phenyl, amino, mono- or disubstituted amino], —C(O)R (where R is hydrogen, alkyl, cycloalkyl, heteroalkyl, haloalkyl or optionally substituted phenyl), —COOR (where R is hydrogen, alkyl, or optionally substituted phenyl), -(alkylene)COOR (where R is hydrogen, alkyl or optionally substituted phenyl), methylenedioxy, 1,2-ethylenedioxy, —CONR'R" or -(alkylene)—CONR'R" (where R' and R" are independently selected from hydrogen, alkyl, cycloalkyl, haloalkyl, cycloalkylalkyl or optionally substituted phenyl). More specifically the term heteroaryl includes, but is not limited to, pyridyl, pyrrolyl, thiophene, pyrazolyl, thiazolyl, imidazolyl, pyrimidinyl, thiadiazolyl, indolyl, carbazolyl, azaindolyl, benzofuranyl, benzotriazolyl, benzisoxazolyl, purinyl, quinolinyl, benzopyranyl, and derivatives thereof.

"Heterocycle" or "Heterocyclyl" means a saturated or unsaturated cyclic radical of 3 to 8 ring atoms in which one or two ring atoms are heteroatoms selected from N, O, or $S(O)_n$ (where n is an integer from 0 to 2). The heterocyclo ring may be optionally substituted independently with one, two or three substituents selected from alkyl, haloalkyl, cycloalkyl, cycloalkylalkyl, aryl, aralkyl, heteroaryl, heteroaralkyl, halo, cyano, acyl, acylamino, amino, mono-substituted amino, disubstituted amino, —COOR (where R is hydrogen or alkyl), —XR (where X is O or S(O)., where n is an integer from 0 to 2 and R is hydrogen, alkyl, haloalkyl, cycloalkyl, aralkyl, aryl, heteroaryl or heteroaralkyl) or —CONR'R" (where R' and R" are independently selected from hydrogen or alkyl). Representative examples include, but are not limited to tetrahydropyranyl, piperidino, 1-(4-chlorophenyl)piperidino, and the like.

"Heteroalkyl" means an alkyl, cycloalkyl, or cycloalkylalkyl radical as defined above, carrying a substituent containing a heteroatom selected from N, O, $S(O)_n$ where n is an integer from 0 to 2. Representative substituents include —$NR^aR^b$, —$OR^a$ or —$S(O)_nR^c$, wherein n is an integer from 0 to 2, $R^a$ is hydrogen, alkyl, haloalkyl, cycloalkyl, cycloalkylalkyl, optionally substituted phenyl, pyridyl, —COR (where R is alkyl or alkoxy) or aminoalkyl, $R^b$ is hydrogen, alkyl, —$SO_2R$ (where R is alkyl or hydroxyalkyl), —$SO_2NRR'$ (where R and R' are independently of each other hydrogen or alkyl), —CONR'R", (where R' and R" are independently selected from hydrogen or alkyl) and $R^c$ is hydrogen, alkyl, cycloalkyl, cycloalkylalkyl, optionally substituted phenyl, amino, mono- or disubstituted amino. Representative examples include, but are not limited to 2-methoxyethyl, benzyloxymethyl, and the like.

"Hydroxyalkyl" means a linear monovalent hydrocarbon radical of two to six carbon atoms or a branched monovalent hydrocarbon radical of three or six carbons substituted with one or two hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl, preferably 2-hydroxyethyl, 2-hydroxypropyl, 3-hydroxypropyl, 2,3-dihydroxypropyl, and 4-hydroxybutyl.

"Aminoalkyl" means an alkyl radical as defined above, carrying one or two amino groups, e,g., 2-arninoethyl, 2-aminopropyl, 3-aminopropyl, 1-(aminomethyl)-2-methylpropyl, and the like.

"Amidoalkyl" means an alkyl radical as defined above, carrying a —$NRCOR^a$ group where R is hydrogen or alkyl and $R^a$ is alkyl as defined above, e,g., —$(CH_2)_2NHCOCH_3$, —$(CH_2)_3NHCOCH_3$, and the like.

"Sulfonylaminoalkyl" means an alkyl radical as defined above, carrying a —$NRSO_2R^a$ group, e,g., —$(CH_2)_2NHSO_2CH_3$, —$(CH_2)_3NHSO_2CH_3$, —$(CH_2)_2NHSO_2C_2H_5$, and the like.

"Carboxyalkyl" means an alkyl radical as defined above, carrying a carboxy group, e,g., carboxymethyl, 2-carboxyethyl, 2-carboxypropyl, 3-carboxypropyl, 1-(carboxymethyl)-2-methyl-propyl, and the like.

"Alkoxycarbonylalkyl" means an alkyl radical as defined above, carrying a —COOR group where R is an alkyl group as defined above, e,g., 2-methoxycarbonylethyl, ethoxycarbonylmethyl, 2-ethoxycarbonylethyl, 3-ethoxycarbonylpropyl, 3-methoxycarbonylpropyl, and the like.

"Alkoxyalkyl" means an alkyl radical as defined above, carrying an alkoxy group, e,g., methoxymethyl, 2-methoxyethyl, 2-methoxypropyl, 3-methoxypropyl, 1-(methoxymethyl)-2-methylpropyl, and the like.

"Cyanoalkyl" means an alkyl radical as defined above, carrying a cyano group, e,g., 2-cyanoethyl, 2-cyanopropyl, 3-cyanopropyl, 1-(cyanomethyl)-2-methylpropyl, and the like.

"Cycloalkylalkyl" means a radical -R $R^b$ where $R^a$ is an alkylene group and $R^b$ is a cycloalkyl group as defined above e.g., cyclopropylmethyl, cyclohexylpropyl, 3-cyclohexyl-2-methylpropyl, and the like.

"Aralkyl" means a radical —$R^a$ $R^b$ where $R^a$ is an alkylene group and $R^b$ is an aryl group as defined above e.g., benzyl, phenylethyl, 3-(3-chlorophenyl)-2-methylpentyl, and the like.

"Heteroaralkyl" means a radical —$R^a$ $R^b$ where $R^a$ is an alkylene group and $R^b$ is a heteroaryl group as defined above e.g., pyridin-3-ylmethyl, 3-(benzofuran-2-yl)propyl, and the like.

"Heterocyclylalkyl" means a radical —$R^a$ $R^b$ where $R^a$ is an alkylene group and $R^b$ is a heterocyclyl group as defined above e.g., tetrahydropyran-2-ylmethyl, 4-methylpiperazin-1-ylethyl, and the like.

"Alkoxy", "haloalkyloxy", "aryloxy", "heteroaryloxy", "aralkyloxy", or "heteroaralkyloxy" means a radical —OR where R is an alkyl, haloalkyl, aryl, heteroaryl, aralkyl, or heteroaralkyl respectively as defined above e.g., methoxy, phenoxy, pyridin-2-yloxy, benzyloxy, and the like.

"Optional" or "optionally" means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

"Amino-protecting group" refers to those organic groups intended to protect nitrogen atoms against undesirable reactions during synthetic procedures e.g., benzyl benzyloxycarbonyl (CBZ), t-butoxycarbonyl (BOC), trifluoroacetyl, and the like.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, where a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the $R^3$ and $R^4$ substituents in a compound of Formula (I) are different, then the carbon to which they are attached is an asymmetric center and the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

A "pharmaceutically acceptable counterion" means an ion having a charge opposite to that of the substance with which it is associated and that is pharmaceutically acceptable. Representative examples include, but are not limited to, chloride, bromide, iodide, methanesulfonate, p-tolylsulfonate, trifluoroacetate, acetate, and the like.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)-benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]oct-2-ene-1-carboxylic acid, glucoheptonic acid, 4,4-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Leaving group" has the meaning conventionally associated with it in synthetic organic chemistry i.e., an atom or group capable of being displaced by a nucleophile and includes halogen, alkanesulfonyloxy, arenesulfonyloxy, ester, or amino such as chloro, bromo, iodo, mesyloxy, tosyloxy, trifluorosulfonyloxy, methoxy, N,O-dimethylhydroxyl-amino, and the like.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, sulfhydryl or amino group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Nomenclature

The nomenclature used in this application is generally based on the IUPAC recommendations, e.g., a compound of Formula (I) where T is —$N^+R^5$—, U is carbon, m is 1, R, $R^1$, $R^2$ and $R^3$ are hydrogen, $R^4$ is 1-methylethyl, $R^5$ is ethyl, X is iodide, E is —NHC(O)NH—, F is a bond, Q is —$CH_2$—, Ar is 3,4,5-trimethoxyphenyl, $Ar^1$ is 3,4-chlorophenyl and the stereochemistry at the carbon to which $R^3$ and $R^4$ are attached is R is named, 4-(3,4-dichlorobenzyl)-1-ethyl-1-{3-methyl-2(R)-[3-(3,4,5-trimethoxyphenyl)ureido]butyl}-piperidinium iodide.

a compound of Formula (I) where T is —$N^+R^5$—, U is carbon, m is 1, R, $R^1$, $R^2$ and $R^3$ are hydrogen, $R^4$ is 1-methylethyl, R is methyl, X is chloride, E is —C(O)NH—, F is a bond, Q is —$CH_2$—, Ar is 4-(2-aminoethyl)phenyl, $Ar^1$ is 3,4-chlorophenyl and the stereochemistry at the carbon to which $R^3$ and $R^4$ are attached is R is named, 1-{2-(R)-[4-(2-arninoethyl)-benzoylamino]-3-methylbutyl}-4-(3,4-dichlorobenzyl)-1-methyl-piperidinium chloride.

Representative compounds of this invention are as follows:

I. Representative compounds of Formula (I) where T=—$N^+R^5$—; U=carbon; m=1; R=$R^1$=$R^2$=$R^3$=hydrogen; F=bond; Q=—$CH_2$—; E=—C(O)NH— and other groups are as defined below are:

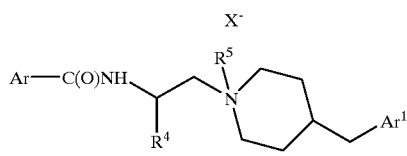

| CPD # | Stereo-chem | Ar | R⁴ | R⁵ | X⁻ | Ar¹ | Mass Spec. m/e |
|---|---|---|---|---|---|---|---|
| 1 | (R) | 4-methylphenyl | 1-methylethyl | methyl | Cl | 3,4-dichlorophenyl | 461 |
| 2 | (R) | 4-methylphenyl | 1-methylethyl | methyl | TFA | 3,4-dichlorophenyl | 461 |
| 3 | (R) | 4-[2-(t-butoxy-carbonylamino)-ethyl)]phenyl | 1-methylethyl | ethyl | I | 3,4-dichlorophenyl | 604 |
| 4 | (R) | 4-(2-aminoethyl)-phenyl | 1-methylethyl | methyl | Cl | 3,4-dichlorophenyl .HCl | 490 |
| 5 | (S) | 4-methylphenyl | 1-methylethyl | methyl | Cl | 3,4-dichlorophenyl | 461 |
| 6 | (R) | 4-(2-aminoethyl)-phenyl | 1-methylethyl | ethyl | Cl | 3,4-dichlorophenyl .HCl | 504 |
| 7 | (S) | 4-[2-(t-butoxy-carbonylamino)-ethyl)]phenyl | 1-methylethyl | ethyl | I | 3,4-dichlorophenyl | 604 |
| 8 | (S) | 4-(2-aminoethyl)-phenyl | 1-methylethyl | ethyl | Cl | 3,4-dichlorophenyl .HCl | 504 |
| 9 | (S) | 4-(2-aminoethyl)-phenyl | 1-methylethyl | ethyl | Cl | 3,4-dichlorophenyl .HCl | 490 |

II. Representative compounds of Formula (I) where T=carbon; U=—N⁺R⁵—; m=0; R=R¹=R²=R³=hydrogen; F=bond; Q=—CH₂—; E=—C(O)NH— and other groups are as defined below are:

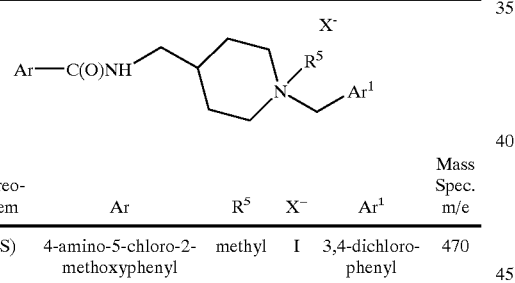

| CPD # | Stereo-chem | Ar | R⁵ | X⁻ | Ar¹ | Mass Spec. m/e |
|---|---|---|---|---|---|---|
| 1 | (RS) | 4-amino-5-chloro-2-methoxyphenyl | methyl | I | 3,4-dichlorophenyl | 470 |

III. Representative compounds of Formula (I) where T=—N⁺R⁵—; U=carbon; m=1; R=R¹=R²=R³=hydrogen; F=bond; Q=—CH₂—; E=—NHC(O)NH— and other groups are as defined below are:

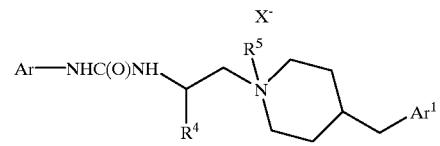

| CPD # | Stereo-chem | Ar | R⁴ | R⁵ | X⁻ | Ar¹ | M.Pt. °C. | Mass Spec. m/e |
|---|---|---|---|---|---|---|---|---|
| 1 | (R) | 3,4,5-trimethoxyphenyl | 1-methylethyl | ethyl | I | 3,4-dichlorophenyl | | 566 |
| 2 | (R) | 3-methoxyphenyl | 1-methylethyl | ethyl | I | 3,4-dichlorophenyl | | 506 |
| 3 | (R) | 3,5-dimethoxyphenyl | 1-methylethyl | ethyl | I | 3,4-dichlorophenyl | | 536 |

-continued

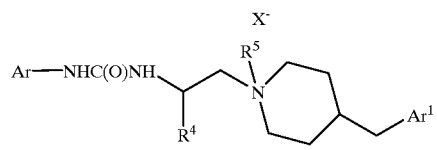

| CPD # | Stereo-chem | Ar | $R^4$ | $R^5$ | $X^-$ | $Ar^1$ | M.Pt. °C. | Mass Spec. m/e |
|---|---|---|---|---|---|---|---|---|
| 4 | (R) | 3-acetylphenyl | 1,1-dimethylethyl | ethyl | I | 3,4-dichlorophenyl | | |
| 5 | (R) | 3,5-dimethoxyphenyl | 1,1-dimethylethyl | ethyl | I | 3,4-dichlorophenyl | | |
| 6 | (R) | 3-acetylphenyl | 1-methylethyl | ethyl | I | 3,4-dichlorophenyl | | 520 |
| 7 | (R) | 3-methoxyphenyl | 1,1-dimethylethyl | ethyl | I | 3,4-dichlorophenyl | | |
| 8 | (R) | 3-methoxycarbonyl-phenyl | 1-methylethyl | ethyl | I | 3,4-dichlorophenyl | | 534 |
| 9 | (R) | 2,5-dimethoxyphenyl | 1,1-dimethylethyl | ethyl | I | 3,4-dichlorophenyl | | |
| 10 | (R) | 2,3,4-trimethoxyphenyl | 1-methylethyl | ethyl | I | 3,4-dichlorophenyl | | 566 |
| 11 | (R) | 3-carboxyphenyl | 1-methylethyl | ethyl | I | 3,4-dichlorophenyl | | 520 |
| 12 | (R) | 2-ethylphenyl | 1,1-dimethylethyl | ethyl | I | 3,4-dichlorophenyl | | |
| 13 | (S) | 3-methoxyphenyl | 1-methylethyl | ethyl | I | 3,4-dichlorophenyl | | 506 |
| 14 | (R) | 3,4,5-trimethoxyphenyl | 1-methylethyl | methyl | I | 3,4-dichlorophenyl | | |
| 15 | (R) | 3-methoxyphenyl | 1-methylethyl | methyl | I | 3,4-dichlorophenyl | | |
| 16 | (R) | 3,4,5-trimethoxyphenyl | 1-methylethyl | 2-hydroxy-ethyl | Cl | 3,4-dichlorophenyl | | |
| 17 | (R) | 3,4,5-trimethoxyphenyl | 1-methylethyl | ethoxycarbonyl methyl | I | 3,4-dichlorophenyl | | |
| 18 | (R) | 3,4,5-trimethoxyphenyl | 1-methylethyl | benzyl | I | 3,4-dichlorophenyl | 131–207 | |
| 19 | (R) | 3,4,5-trimethoxyphenyl | H | methyl | I | 3,4-dichlorophenyl | 102–108 | |
| 20 | (R) | 3,4,5-trimethoxyphenyl | 1-methylethyl | ethyl | I | 3,4-dichlorophenyl | | |
| 21 | (R) | 3,4,5-trimethoxyphenyl | 1-methylethyl | methyl | I | 3,4-dichlorophenyl | 123.7–138 | |
| 22 | (R) | 3,4,5-trimethoxyphenyl | 1-methylethyl | carboxymethyl | I | 3,4-dichlorophenyl | | |

PREFERRED EMBODIMENTS

While the broadest definition of this invention is set forth in the Summary of the Invention, certain compounds of Formula (I) are preferred.

(I) A preferred group of compounds is that wherein:
T is —N$^+$R$^5$— wherein R$^5$ is alkyl, hydroxyalkyl, alkoxycarbonylalkyl, preferably methyl, ethyl, 2-hydroxyethyl, 3-hydroxypropyl, methoxycarbonylmethyl, ethoxycarbonylmethyl, most preferably methyl, ethyl, or 2-hydroxyethyl;
m is 1;
R, R$^1$, R$^2$ and R$^3$ are hydrogen;
F is a bond;
Q is an alkylene chain, more preferably methylene or ethylene, most preferably methylene.

(A) Within this group (I), a more preferred group of compounds is that wherein:
E is —C(O)NH—; and
R$^4$ is alkyl or heteroalkyl, preferably 1-methylethyl, 1,1-dimethylethyl, 2-methylpropyl, 3-hydroxypropyl, 1-hydroxyethyl or 2-hydroxyethyl, more preferably 1-methylethyl or 1,1-dimethylethyl.

Within the preferred and more preferred groups, an even more preferred group of compounds is that wherein:
The stereochemistry at the carbon atom to which the R$^3$ and R$^4$ groups are attached is (R);
Ar is a heteroaryl or aryl ring, preferably a pyridin-2-yl, pyridin-3-yl, quinolin-3-yl or 5-methylthiophen-2-yl ring or a phenyl ring optionally substituted with one, two or three substituent(s) selected from alkyl, heteroalkyl, alkoxy, —COR (where R is alkyl), —SO$_2$R (where R is alkyl, amino or mono or disubstituted amino), methylenedioxy, hydroxy, halo, acylamino, amino, mono- or disubstituted amino, —CONR'R", -(alkylene)—CONR'R" (where R' and R" are hydrogen or alkyl), —COOR, -(alkylene)—COOR (where R is hydrogen or alkyl) or —NRSO$_2$R' (where R is hydrogen or alkyl and R' is alkyl, amino, mono or disubstituted amino), more preferably a phenyl ring optionally substituted with one, two or three substituent (s) selected from methyl, methoxy, fluoro, chloro, dimethylamino, acetyl, hydroxy, amino, methylenedioxy, —SO$_2$Me, 2-acetylaminoethyl, 2-[(R)-amino-3-methylbutyrylamino]ethyl, 2-aminoethyl, aminomethyl, hydroxymethyl, aminocarbonyl, dimethylaminocarbonyl, —COOH, carboxymethyl, methoxycarbonylmethyl, aminocarbonylmethyl, dimethylaminocarbonylmethyl, acetylaminomethyl, methylsulfonylamino, methylsulfonylamninomethyl, dimethylaminosulfonylaminomethyl, or dimethylamino, most preferably phenyl, 4-chlorophenyl, 3,4-difluorophenyl, 4-methylphenyl, 4-methoxyphenyl, 4-hydroxyphenyl, 4-dimethylaminophenyl, 4-aminocarbonylphenyl, 4-acetylphenyl, 4-acetylaminophenyl, 3,4-methylenedioxyphenyl, 4-methylsulfonylphenyl, 4-[(2-acetylamino)ethyl]phenyl, 4-{2-[(R)-amino-3-methylbutyrylamino]ethyl}phenyl, 4-(2-arninoethyl) phenyl, 4-(aminomethyl)phenyl, 4-(hydroxymethyl) phenyl, 2,5-dimethoxyphenyl, 3,5-dimethoxy-phenyl, 3,4-dimethoxyphenyl, 3,4,5-trimethoxyphenyl, 4-aminocarbonyl-methylphenyl, 4-acetylaminomethyphenyl, 4-methylsulfonylaminophenyl, 4-methylsulfonylamino-methylphenyl or 4-aminophenyl; and $Ar^1$ is a heteroaryl or aryl ring, preferably 1-acetylindol-3-yl, 3-methylbenzo-thiophen-2-yl, 5-nitrothiophen-3-yl or a phenyl ring optionally substituted with one, two or three substituent(s) selected from alkyl, heteroalkyl, alkoxy, halo, trifluoromethyl, nitro, or mono- or disubstituted amino, more preferably a phenyl ring substituted with one or two substituents selected from methyl, methoxy, chloro, fluoro, trifluoromethyl or nitro, most preferably 4-nitrophenyl, 4-trifluoromethylphenyl, 4-chlorophenyl, 3,4-difluorophenyl, 2,3-dichlorophenyl, 3-methyl-4-nitrophenyl, 3-chloro-4-fluorophenyl or 3,4-dichlorophenyl.

(B) Another more preferred group of compounds within group (I) is that wherein:

E is —NHC(O)NH—; and $R^4$ is alkyl or heteroalkyl, preferably 1-methylethyl, 1,1-dimethylethyl, 2-methylpropyl, 3-hydroxypropyl, 1-hydroxyethyl or 2-hydroxyethyl, more preferably 1-methylethyl or 1,1-dimethylethyl.

Within the preferred and more preferred groups, an even more preferred group of compounds is that wherein:

The stereochemistry at the carbon atom to which the $R^3$ and $R^4$ groups are attached is (R);

Ar is a heteroaryl or aryl ring, preferably a pyridin-2-yl, pyridin-3-yl, quinolin-3-yl or 5-methylthiophen-2-yl ring or a phenyl ring optionally substituted with one, two or three substituent(s) selected from alkyl, heteroalkyl, alkoxy, —COR (where R is alkyl), —$SO_2$R (where R is alkyl, amino or mono or disubstituted arnino), methylenedioxy, hydroxy, halo, acylarino, amino, mono- or disubstituted amino, —CONR'R", -(alkylene)—CONR'R" (where R' and R" are hydrogen or alkyl), —COOR, -(alkylene)—COOR (where R is hydrogen or alkyl) or —$NRSO_2$R' (where R is hydrogen or alkyl and R' is alkyl, amino, mono or disubstituted amino), more preferably a phenyl ring optionally substituted with one, two or three substituent(s) selected from methyl, methoxy, fluoro, chloro, dimethylamino, acetyl, acetylamino, hydroxy, amino, methylenedioxy, —$SO_2$Me, 2-acetylaminoethyl, 2-[(R)-amino-3-methylbutyrylaminolethyl, 2-aminoethyl, aminomethyl, hydroxymethyl, aminocarbonyl, dimethylarninocarbonyl, —COOH, carboxymethyl, methoxycarbonylmethyl, aminocarbonylmethyl, dimethylaminocarbonylmethyl, acetylarninomethyl, methylsulfonylamino, methylsulfonylaminomethyl, dimethylaminosulfonylaminomethyl, or dimethylamino, most preferably phenyl, 3-methoxyphenyl, 3-methylsulfonylphenyl, 3-dimethylarninophenyl, 3-acetylaminophenyl, 3-acetylphenyl, 3-[(2-acetylamino) ethyl]-phenyl, 3-aminocarbonylphenyl, 3-carboxyphenyl, 2,5-dimethoxyphenyl, 3,5-dimethoxyphenyl, 3,4-dimethoxyphenyl, 3,4,5-trimethoxyphenyl, 3-aminocarbonylmethylphenyl, 3-dimethylaminocarbonylphenyl, 3-acetylaminomethyphenyl, 3-carboxymethylphenyl, 3-methylsulfonylaminophenyl, 3-methylsulfonylaminomethylphenyl or 3-aminophenyl; and $Ar^1$ is a heteroaryl or aryl ring, preferably 1-acetylindol-3-yl, 3-methylbenzo-thiophen-2-yl, 5-nitrothiophen-3-yl or a phenyl ring optionally substituted with one, two or three substituent(s) selected from alkyl, heteroalkyl, alkoxy, halo, trifluoromethyl, nitro, or mono- or disubstituted amino, more preferably a phenyl ring substituted with one or two substituents selected from methyl, methoxy, chloro, fluoro, trifluoromethyl or nitro, most preferably 4-nitrophenyl, 4-trifluoromethylphenyl, 4-chlorophenyl, 3,4-difluorophenyl, 2,3-dichlorophenyl, 3-methyl-4-nitrophenyl, 3-chloroAfluorophenyl or 3,4-dichlorophenyl.

(II) Another preferred group of compounds is that wherein:

$R^4$ is alkyl or heteroalkyl, preferably 1-methylethyl, 1,1-dimethylethyl, 2-methylpropyl, 3-hydroxypropyl, 1-hydroxyethyl or 2-hydroxyethyl, more preferably 1-methylethyl or 1,1-dimethylethyl.

(III) Yet another preferred group of compounds is that wherein:

E is —C(O)N($R^6$)— or —N($R^7$)C(O)N($R^6$)—, preferably —C(O)NH— or —NHC(O)NH—.

GENERAL SYNTHETIC SCHEME

The compounds of the present invention can be prepared in a number of ways known to one skilled in the art. Preferred methods include, but are not limited to, the general synthetic procedures described below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as *Fieser and Fieser's Reagentsfor Organic Synthesis*, Volumes 1–15 (John Wiley and Sons, 1991); *Rodd's Chemistry of Carbon Compounds*, Volumes 1–5 and Supplementals (Elsevier Science Publishers, 1989), *Organic Reactions*, Volumes 140 (John Wiley and Sons, 1991), *March's* Advanced Organic Chemistry, (John Wiley and Sons, 1992), and *Larock's* Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Synthesis of Compounds of Formula (I)

In general, compounds of Formula (I) where m, R, $R^1$, $R^2$, $R^3$, $R^4$, $R^5$, Q, Ar and $Ar^1$ are as defined in the Summary of the Invention are prepared by converting aminoalkyl derivatives of Formulae II(a–b) and carboxyalkyl derivatives of Formulae II(c–d) to a compound of Formula (Ia) which is then converted to the quartemary salt of Formula (I) as shown in FIG. 1 below.

FIG. 1

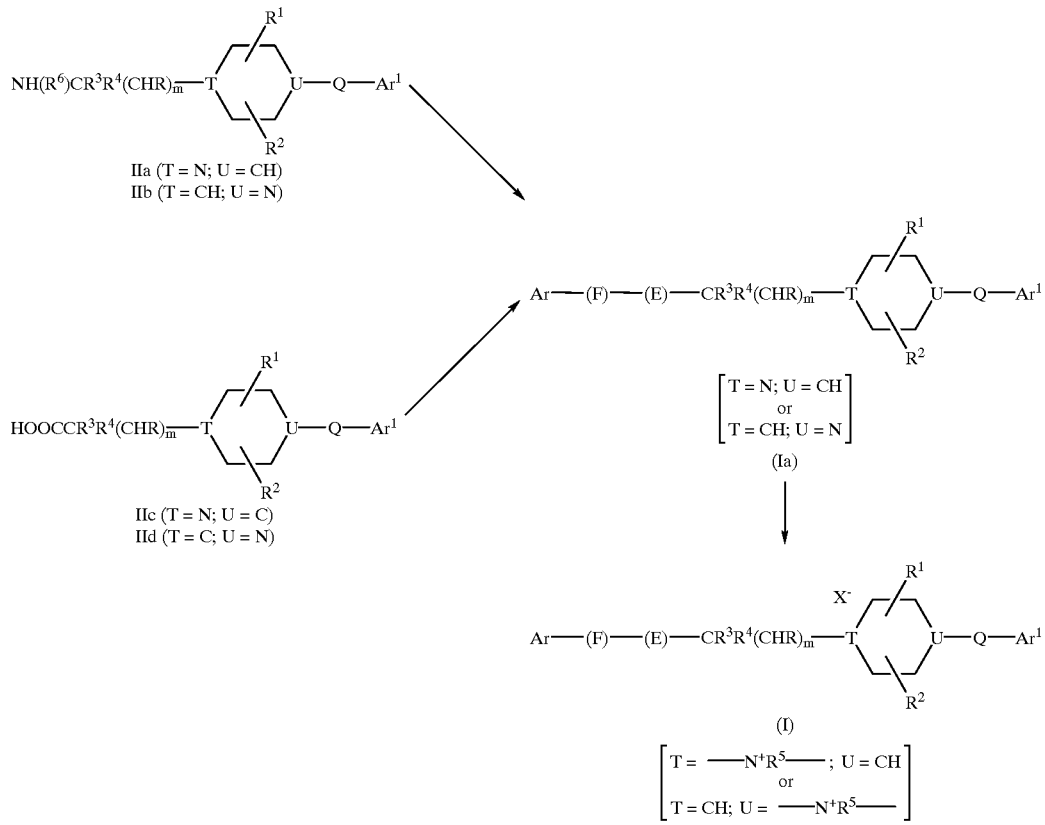

Synthesis of compounds of Formulae II (a–d) and their conversion to compounds of Formulae (Ia) and (I) are described in detail in Schemes A-J below. Synthesis of compounds of Formula (Ia) is also described in copending U.S. patent application Ser. No. 09/134,013, filed Aug. 14, 1998 whose disclosure is hereby incorporated by reference.

Synthesis of compounds of Formulae 11(a–d)

Preparation of Compounds of Formula (IIa)

A compound of Formula (IIa) where T is nitrogen, m is at least 1 and R, $R^1$, $R^2$, $R^3$, $R^4$, $R^6$, Q and $Ar^1$ are as defined in the Summnary of the invention is prepared as illustrated in Scheme A below.

Scheme A

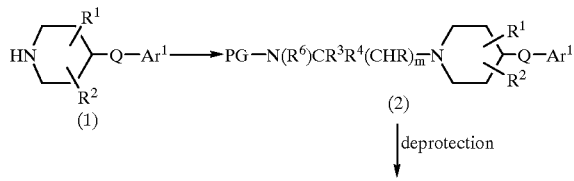

-continued

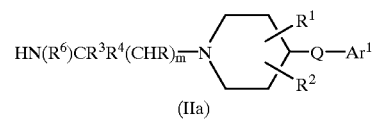

In general, compounds of Formula (IIa) are prepared in two steps by first converting a compound of formula 1 to an N-protected aminoalkyl derivative of formula 2, followed by removal of the arnino protecting group in 2, as described in detail below.

An N-protected arinoalkyl derivative of formula 2 [where PG is an amino protecting group (e.g., tert-butoxycarbonyl (BOC), benzyloxycarbonyl (CBZ), benzyl, and the like) and $R^6$ is hydrogen] is prepared by reacting a compound of formula 1 with a compound of formula 3

$$PG-N(R^6)CR^3R^4(CHR)_{m-1}X \qquad (3)$$

where X is an aldehyde, ketone (X=—C(O)R where R is alkyl), carboxy or a reactive carboxy derivative e.g., acid halide. The reaction conditions employed for the preparation of 2 depend on the nature of the X group. If X is an aldehyde or a ketone group, the reaction is carried out under reductive amination reaction conditions i.e., in the presence of a suitable reducing agent (e.g., sodium cyanoborohydride, sodium triacetoxyborohydride, and the like) and an organic acid (e.g., glacial acetic acid, trifluoroacetic acid, and the like) at ambient temperature. Suitable solvents for the reaction are halogenated hydrocarbons (e.g., 1,2-dichloroethane, chloroform, and the like). If X is a carboxy group, the reaction is carried out in the presence of a suitable coupling agent (e.g., N,N-dicyclohexylcarbodiimnide, 1-(3-dimethylaminopropyl)-3-ethylcarbodiimide, and the like) in a suitable organic solvent (e.g., methylene chloride, tetrahydrofuran, and the like) to give an amide intermediate. Reduction of the amide intermediate with a suitable reducing agent (e.g., diborane, lithium aluminum hydride, and the like) in an ethereal organic solvent such as ether or tetrahydrofuran then provides a compound of formula 2. If X is an acid derivative such as an acid chloride, the reaction is carried out in the presence of a suitable base such as triethylamine, pyridine in an organic solvent (e.g., methylene chloride, dichloroethane, N,N-dimethylformamide, and the like) to give an amide intermediate which is reduced to compound 2 as described above.

In general, compounds of formula 3 are commercially available or they can be prepared by methods well known in the field of organic chemistry. Some examples of such procedures are illustrated and described in detail below.

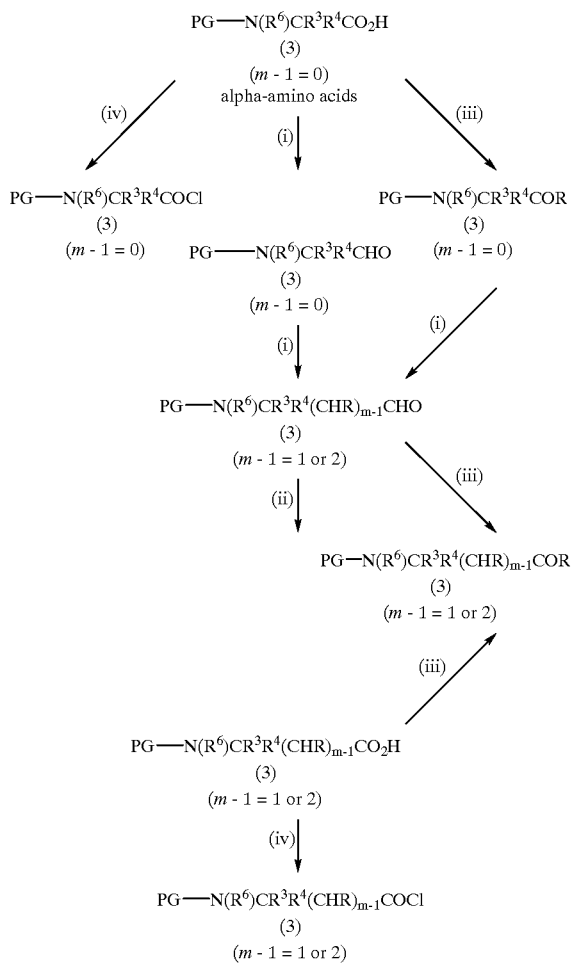

(i) An aldehyde of formula 3 (X is a —CHO, and m−1=0) is conveniently prepared from the corresponding natural or unnatural α-amino acid of formula 3 where X is a carboxy group and m−1=0 by first converting the α-amino acid to the corresponding ester followed by reduction of the ester group to an aldehyde group with a suitable reducing agent such as DIBAL-H®. An aldehyde of formula 3 where m−1=1 or 2 can be prepared, if desired, from an aldehyde or ketone (X=—COR where R is alkyl) of formula 3 where m−1=0 under Wittig reaction conditions. For example, an aldehyde 3 where m−1=1 and R is hydrogen or alkyl is prepared by condensing the corresponding aldehyde or ketone of formula 3 where m−1=0 with a Wittig reagent derived from chloromethyl methyl ether, followed by acidic hydrolysis of the resulting enol ether intermnediate. An aldehyde 3 where m−1=2 and R are hydrogen or alkyl can be prepared by condensing the corresponding aldehyde or ketone 3 where m−1=0 with a Wittig reagent derived from bromoacetate or 2-bromopropionate respectively, followed by sequential reduction of the double bond and the ester group in the resulting α,β-unsaturated ester. The ketone of formula 3 where m−1=0 can be prepared from the α-amino acids of formula 3 by converting the α-amino acids 3 to a Weinreb amide, followed by treatment with a Grignard reagent of formula RMgBr where R is an alkyl group. Alternatively, the aldehyde can be prepared by oxidation of the hydroxy group in an α-amino alcohol such as 2-amnino-1-propanol, and the like.

Generally, both natural and unnatural amino acids and their corresponding esters are commercially available from vendors such as Aldrich and Bachem. Examples of unnatural amino acids include, homoserine, homocysteine, N-α-methylarginine, norleucine, N-methylisoleucine, phenylglycine, hydroxyproline, pyroglutamine, ornithine, 2-aminoisobutyric acid, 2-aminobutyric acid, β-cyclohexylalanine, 3-(1-naphthyl)alanine, 3-(2-naphthyl) alanine, citrulline, pipecolinic acid, piperazic acid, 4-chlorophenylalanine, 4-fluorophenylalanine, sarcosine, serine ethyl ester, and alanine methyl ester are commercially available.

(ii) Compounds of formula 3 where X is a carboxy group and m−1>0 can be prepared from the corresponding aldehyde of formula 3 (X is —CHO), prepared as described in (i) above, by oxidation of the aldehyde group with a suitable oxidizing agent (e.g., potassium permanganate, and the like). Alternatively, they can be prepared from the α,β-unsaturated ester formed in the Wittig reaction, see (i) above, by reduction of the double bond, followed by the hydrolysis of the ester group by methods well known in the art.

(iii) Compounds of formula 3 where X is —C(O)R (where R is alkyl) and m−1=0, 1 or 2 can be prepared by alkylating the corresponding aldehyde of formula 3 (X is —CHO) with a Grignard reagent, followed by oxidation of the resulting alcohol with a suitable oxidizing agent such as potassium permanganate, and the like. Alternatively, they can be prepared from the corresponding acid of formula 3 as described in (i) above.

(iv) Compounds of formula 3 where X is an acid derivative e.g., an acid chloride can be prepared from the corresponding acids of formula 3 (X is —COOH), prepared as described in (iii) above, by chlorinating the carboxy group with a suitable chlorinating agent (e.g., oxalyl chloride, thionyl chloride and the like) in a suitable organic solvent such as methylene chloride and the like.

Alternatively, a compound of formula 2 can also be prepared by reacting a compound of formula 1 with an alkylating agent of formula 4

$$PG—N(R^6)CR^3R^4(CHR)_mY \qquad 4$$

where Y is a leaving group under alkylating conditions such as halo (e.g., chloro, bromo or iodo) or sulfonyloxy group (e.g., methylsulfonyloxy or 4-methylphenylsulfonyloxy or trifluoromethylsulfonyloxy). The reaction is carried out in the presence of a base such as sodium carbonate, sodium hydride, triethylarnine and the like. Suitable solvents are aprotic organic solvents such as tetrahydrofuran, N,N-dimethylfoimamide, and the like.

In general, compounds of formula 4 where Y is a halo or a sulfonyloxy group can be prepared from compounds of formula 3 by reducing an aldehyde, ketone or carboxy group to an alcohol, followed by treatment with a suitable halogenating agent (e.g., thionyl chloride, thionyl bromide, carbon tetrabromide in the presence of triphenylphosphine, and the like) or sulfonylating agent (e.g., methylsulfonyl chloride, para-toluenesulfonyl chloride and triflic anhydride) respectively. Suitable aldehyde, ketone and carboxy group reducing agents include lithium aluminum hydride, borane, and the like.

In some instances, a compound of Formula (IIa) can be prepared by reacting a compound of formula 1 with a conjugated nitro-olefin under Michael addition reaction conditions, followed by reduction of the nitro group under standard hydrogenation reaction conditions. Conjugated nitro-olefins are commercially available or can be prepared by known literature procedures e.g., see Corey, E. J. et al., *J. Am. Chem. Soc*, 100(19), 8294–5, (1978).

The N-protected aminoalkyl derivative 2 is converted to a compound of Formula (IIa) by removal of the amino protecting group. The conditions utilized depend on the nature of the protecting group. For example, if the protecting group is the tert-butoxycarbonyl group it is removed under acidic hydrolysis reaction condition whereas if it is the benzyl group it is removed under catalytic hydrogenation reaction conditions.

A compound of Formula (IIa) where $R^6$ is other than hydrogen can be prepared, if desired, by alkylating the corresponding compound of Formula (IIa) where $R^6$ is hydrogen with an alkylating agent $R^6Y$ where Y is a leaving group under alkylating conditions, utilizing the reaction conditions described above.

Compounds of formula 1 can be prepared from suitably N-protected piperidinones by known procedures. Some examples of such procedures are described below:

(i) Compounds of formula 1 where Q is —C(O)— or an alkylene chain are prepared by reacting a suitably N-protected4piperidinone with a Wittig reagent Br⁻(Ph)$_3$P$^+$-alkylene-Ar$^1$ to give an alkylidene intermediate. Treatment of the alkylidene intermediate with borane, followed by oxidation of the resulting alkylborane with an oxidizing agent such as chromic acid under the reaction conditions described in Brown, Garg *J. Am. Chem. Soc.* 83, 2951 (1961) and removal of the N-protecting group provides a compound of formula 1 where Q is —CO—. Reduction of the olefinic bond in the alkylidene intermediate followed by removal of the N-protecting group provides compounds of formula 1 where Q is an alkylene chain. A detailed description of the synthesis of a piperidine of formula 1 by this method where Q is an alkylene chain is given in Example 1.

(ii) Compounds of formula 1 where Q is —O-alkylene-Ar$^1$ can be prepared by reacting a 4-hydroxypiperidine with an alkylating agent of formula Ar$^1$—Q—Y where Y is a leaving group under alkylating reaction conditions as defined previously.

(iii) Compounds of formula 1 where Q is —NH—alkylene-Ar$^1$ can be prepared by reacting an N-protected-4-piperidone with an amine of formula NH$_2$-alkylene-Ar$^1$ under reductive amination reaction conditions as described previously.

4-hydroxypiperidine and 4-piperidinone are commercially available.

Preparation of Compounds of Formula (IIb)

A compound of Formula (IIb) where U is nitrogen, m is 1 and R, $R^1$, $R^2$, $R^3$, $R^4$, $R^6$, Q and Ar$^1$ are as defined in the Summary of the invention can be prepared from a compound of formula 5 as illustrated in Scheme B below.

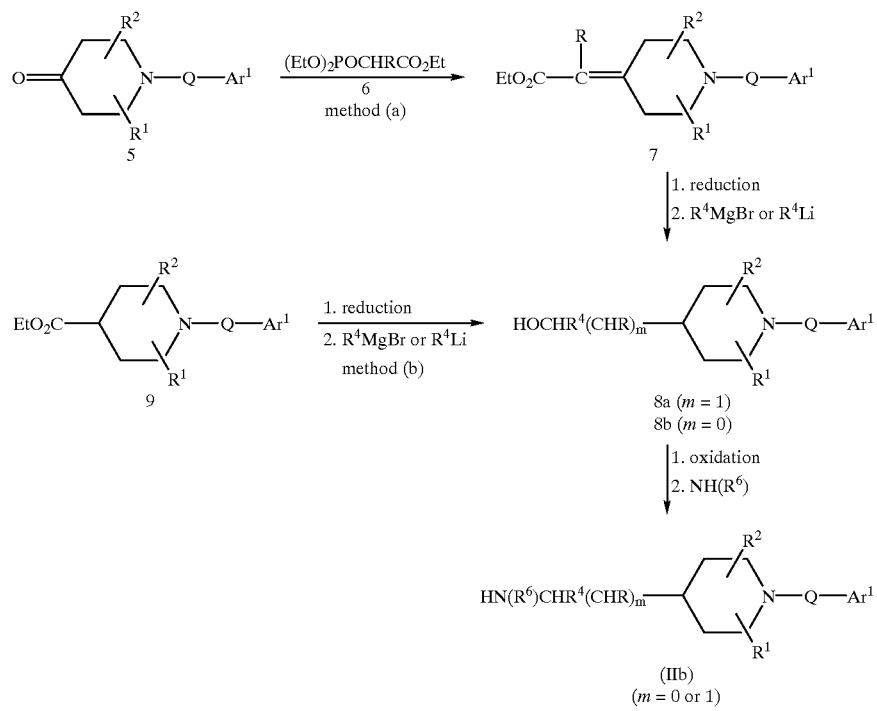

Scheme B

A compound of Formula (IIb) where m is 1 can be prepared, as shown in method (a), by reacting a compound of formula 5 with a phosphonate ylide of formula 6 under Wittig reaction conditions, i.e., in the presence of a strong non-nucleophilic base (e.g., sodium hydride, sodium amide, and the like) and in a suitable aprotic organic solvent (e.g., tetrahydrofuran and the like) to give an α,β-unsaturated ester of formula 7. The α,β-unsaturated ester 7 is converted to the corresponding alcohol derivative 8a (m=1) by first converting 7 to an aldehyde, followed by treatment with an organometallic reagent such as a Grignard reagent or an organolithium reagent of formula $R^4MgBr$ or $R^4Li$, respectively. The double bond is reduced under hydrogenation reaction conditions and the ester group is reduced to the aldehyde group with a suitable reducing agent such as DIBAL-H®. The alcohol 8a is then converted to a compound of Formula (IIb) by oxidation of the alcohol group to the ketone group, followed by treatment with an amine of formula $NH(R^6)$ under reductive arnination reaction conditions. The oxidation reaction is carried in with a suitable oxidizing reagents such as pyridinium dichromate in an aprotic solvent such as dimethylformamide and the like.

A compound of Formula (IIb) where m is 0 can be prepared, as shown in method (b) from a compound of formula 9, by converting 9 to the corresponding alcohol derivative 8b (m=0) by reduction of the ester group to the aldehyde followed by treatment with a suitable organometallic reagent. Compound 8b is then converted to a compound of Formula (IIb) where m is 0 by carrying out the oxidation and reductive anination steps, utilizing the reaction conditions described above. Compounds of Formula (IIb) where m is 0 can also be prepared by the procedures described in PCT application Publication No. WO 92/12128.

Compounds of formula 5 or 9 can be prepared by N-alkylating a 4-piperidone or ethyl isonipecotate with a compound of formula $Ar^1$—Q—Y where Y is a leaving group under alkylating conditions as described in Scheme A above.

Preparation of Compounds of Formulae (IIc)

A carboxyalkyl derivative of Formula (IIc) where T is nitrogen, m, $R^1$, $R^2$, $R^3$, $R^4$, Q and $Ar^1$ are as defined in the Summary of the invention can be prepared from a compound of formula 1 as illustrated in Scheme C below.

A carboxy derivative of Formula (IIc) is prepared, as shown above, by reacting a compound of formula 1 with an alkylating agent of formula 10 where Y is halo or sulfonyloxy group, followed by hydrolysis of the ester group. The alkylation reaction is carried under the reaction conditions described previously ((see scheme A). The hydrolysis of the ester group is carried out in the presence of an aqueous base (e.g., sodium hydroxide, lithium hydroxide, and the like) in an alcoholic organic solvent such as methanol, ethanol, and the like. The reaction proceeds either at ambient temperature or upon heating. Alternatively, a carboxyethyl derivative of Formula (IIc) where $R^3$ is hydrogen is prepared by reacting a compound of formula 1 with an oc,-unsaturated ester of formula 11 under Michael addition reaction conditions i.e., in the presence of a suitable base such as methoxide and in a protic organic solvent (e.g., methanol, ethanol and the like) to give a 3-propionate derivative of formula 12. Hydrolysis of the ester group in 12 then provides the corresponding carboxyethyl derivative of Formula (IIc) where $R^3$ is hydrogen.

Compounds of formula 1 are prepared as described previously in Schemes A. Compounds of formula 10 and 11 are either commercially available or can be prepared by methods known in the art. For example, halo acids and α,β-unsaturated ester such as methyl 2-bromo-2-methylpropionate, methyl 2-bromopropionate, methyl 3-bromo-2-methylpropionate, methyl α-bromophenylacetate, methyl methacrylate are commercially available.

Preparation of Compounds of Formula (IId)

A carboxyalkyl derivative of Formula (IId) where U is nitrogen, m, $R^1$, $R^2$, $R^3$, $R^4$, Q and $Ar^1$ are as defined in the Summary of the invention can be prepared from a compound of formula 5 or 13 respectively, as illustrated in Scheme D below.

Scheme C

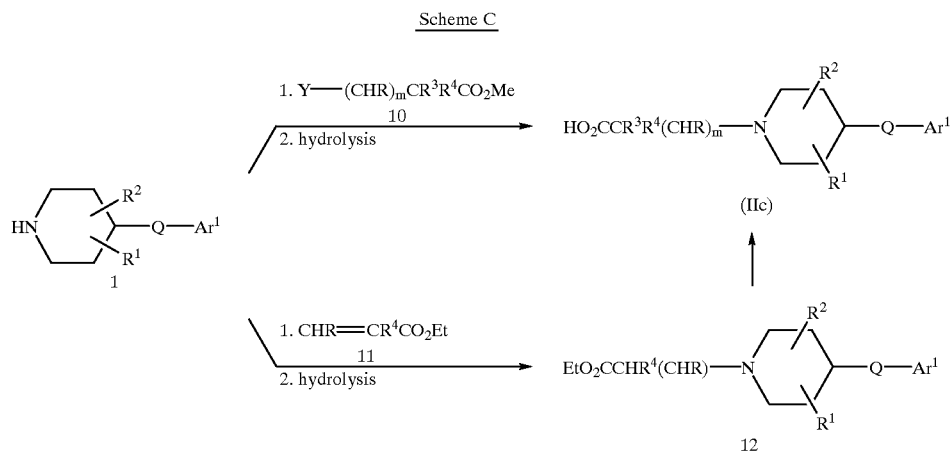

Scheme D

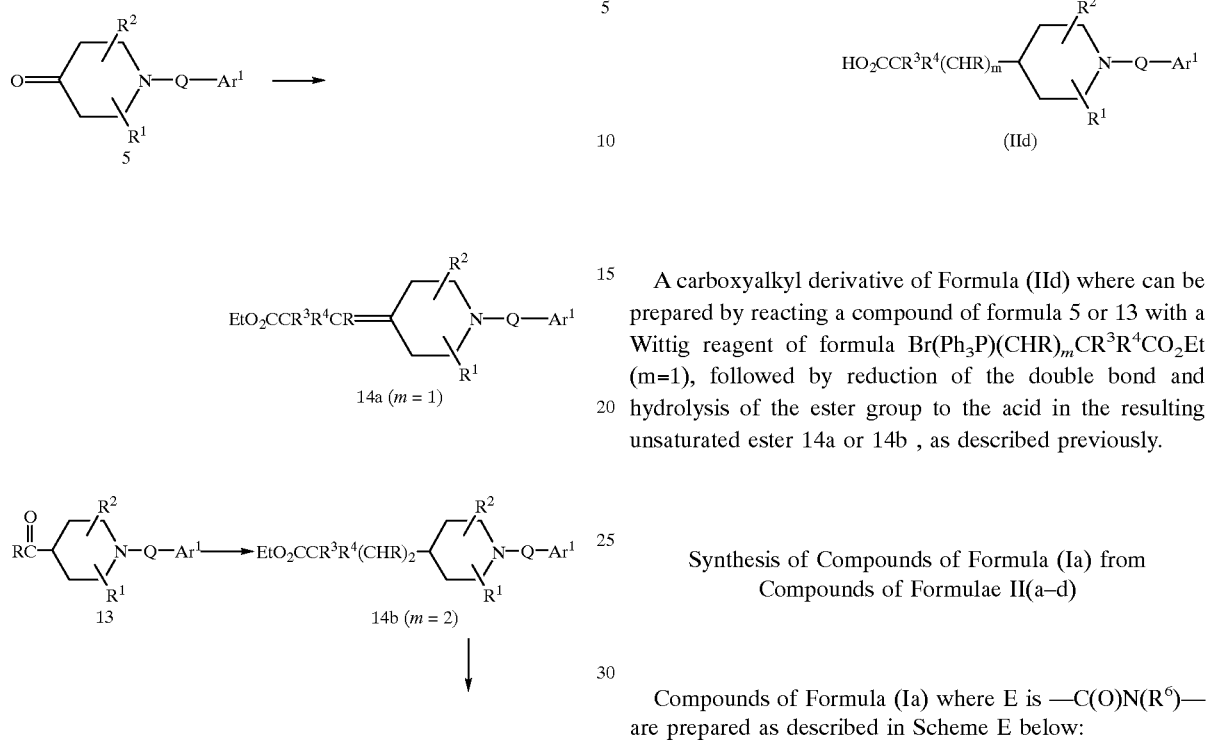

A carboxyalkyl derivative of Formula (IId) where can be prepared by reacting a compound of formula 5 or 13 with a Wittig reagent of formula $Br(Ph_3P)(CHR)_m CR^3R^4CO_2Et$ (m=1), followed by reduction of the double bond and hydrolysis of the ester group to the acid in the resulting unsaturated ester 14a or 14b, as described previously.

Synthesis of Compounds of Formula (Ia) from Compounds of Formulae II(a–d)

Compounds of Formula (Ia) where E is —C(O)N(R⁶)— are prepared as described in Scheme E below:

Scheme E

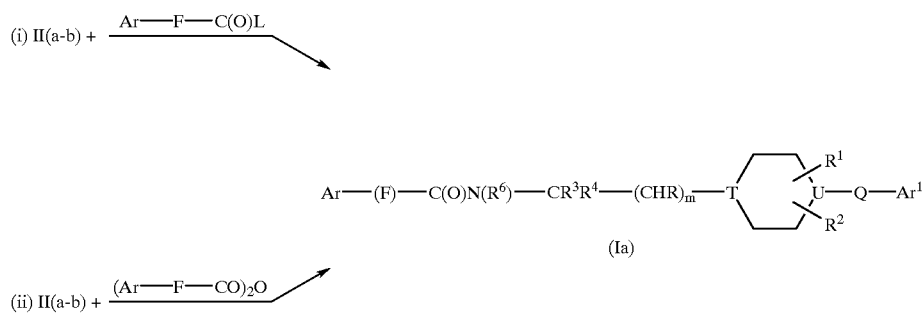

A compound of Formula (Ia) where E is an amide group can be prepared, either:

(i) by reacting a compound of Formula II(a–b) with an acylating reagent Ar—F—C(O)L, where L is a leaving group under acylating conditions, such as a halo (particularly Cl or Br) or imidazolide. Suitable solvents for the reaction include aprotic polar solvents (e.g., dichloromethane, THF, dioxane and the like). When an acyl halide is used as the acylating agent the reaction is carried out in the presence of a non-nucleophilic organic base (e.g., triethylamine or pyridine, preferably pyridine); or (ii) by heating a compound of Formula II(a–b) with an acid anhydride. Suitable solvents for the reaction are tetrahydrofuran, dioxane and the like.

Compounds of Formula (Ia) where E is —N(R$^7$)C(O)N(R$^6$)— or —N(R$^7$)C(S)N(R$^6$)— are prepared as described in Scheme F below:

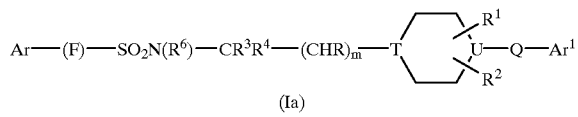

(Ia)

A compound of Formula (Ia) where E is a sulfonamido group can be prepared by reacting a compound of Formula II(a–b) with a sulfonyl halide, utilizing the reaction conditions described in method (i) of Scheme E. Sulfonyl halides are commercially available or may be prepared by methods such as those described in (1) Langer, R. F.; *Can. J. Chem.* 61, 1583–1592, (1983); (2) Aveta, R.; et. al.; *Gazetta Chimica Italiana*, 116, 649–652, (1986); (3) King, J. F. and Hillhouse, J. H.; Can. J. Chem.; 54, 498, (1976); and (4) Szymonifka, M. J. and Heck, J. V.; *Tet. Lett.*; 30, 2869–2872, (1989).

Scheme F

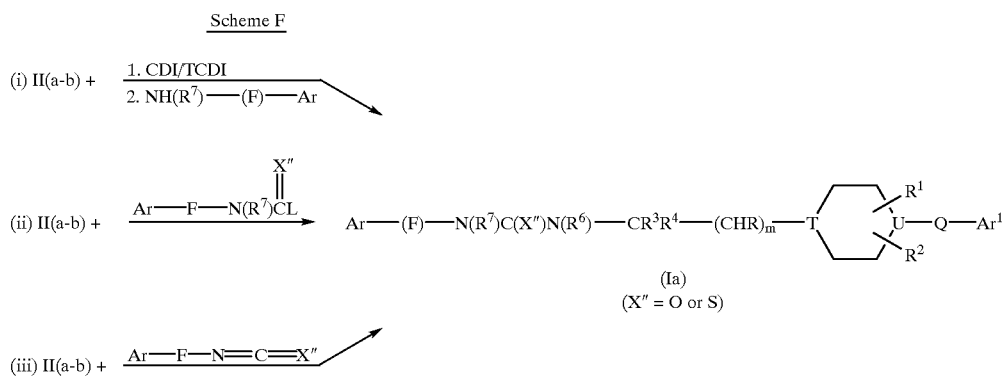

A compound of Formula (Ia) where E is a urea/thiourea group can be prepared, either:

(i) by reacting a compound of Formula II (a–b) with an activating agent such as carbonyl diimidazole/thiocarbonyl diimidazole, followed by nucleophilic displacement of the imidazole group with a primary or secondary amine. The reaction occurs at ambient temperature. Suitable solvents include polar organic solvents (e.g., tetrahydrofuran, dioxane and the like);

(ii) by reacting a compound of Fonnula II (a–b) with a carbamoyllthiocarbamoyl halide. The reaction is carried out in the presence of a non-nucleophilic organic base. Suitable solvents for the reaction are dichloromethane, 1,2-dichloroethane, tetrahydrofuran or pyridine; or (iii) by reacting a compound of Formula II (a–b) with an isocyanate/isothiocyanate in an aprotic organic solvent (e.g., benzene, tetrahydrofuran, dimethylformamide and the like).

A detailed description of the conversion of a compound of Formula (IIa) to a compound of Formula (Ia) where E is —NHC(O)NH— is given in Example 1.

Compounds of Formula (Ia) where E is —SO$_2$N(R$^6$)— are prepared as described in Scheme G below:

Scheme G

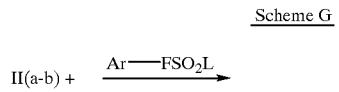

Compounds of Formula (Ia) where E is —N(R$^7$)SO$_2$N(R$^6$)— are prepared as described in Scheme H below:

Scheme H

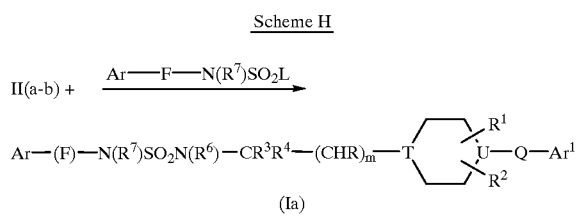

(Ia)

A compound of Formula (Ia) where E is a sulfamide group can be prepared by reacting a compound of Formula It (a–b) with a sulfamoyl halide, utilizing the reaction conditions described in method (i) of Scheme E. Sulfamoyl halides are commercially available or may be prepared by methods such as those described in Graf, R; *German Patent*, 931225 (1952) and Catt, J. D. and Matler, W. L; *J. Org. Chem.*, 39, 566–568, (1974).

Compounds of Formula (Ia) where E is —N(R$^7$)C(O)— are prepared as described in Scheme I below:

Scheme I

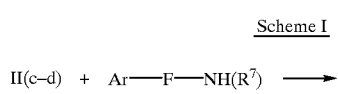

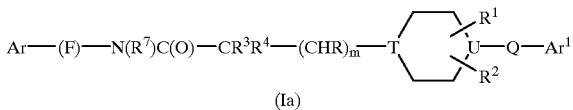

(Ia)

A compound of Formula (Ia) where E is an inverse amide can be prepared by reacting a compound of Formula II(c–d) with an amine in the presence of a suitable coupling agent (e.g., N,N-dicyclohexylcarbodiimide, 1-(3-dimethylaminopropyl)-3-ethylcarbodiimide, and the like) in a suitable organic solvent such as methylene chloride, tetrahydrofuran, dimethylformamide and the like.

Syvnthesis of a Compounds of Formula (I) from a compound of Formula (Ia)

A compound of Formula (I) where T or U is —N$^+$R$^5$— can be prepared from a compound of Formula (Ia) as shown in Scheme J below.

Scheme J

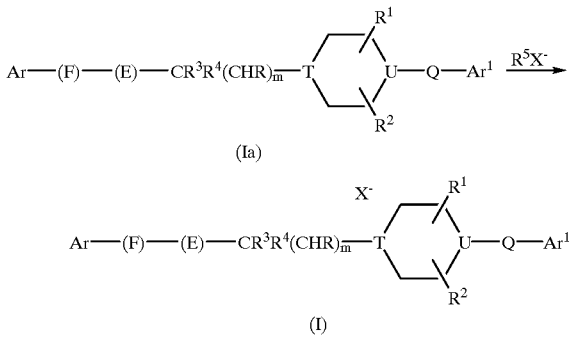

A compound of Formula (Ia) is converted to a compound of Formula (I) where T or U is —N$^+$R$^5$— by reacting it with an alkylating agent of formula R$^5$X where R$^5$ is as defined in the Summary of the Invention and X is a leaving group such as halo (bromide or iodide, preferably iodide), tosylate, mesylate, and the like. Alkylating agents such as methyl iodide, ethyl iodide, ethyl toluenesulfonate, 2-hydroxyethyl iodide and the like are commercially available.

A compound of Formula (I) where X$^-$ is iodide can be converted to a corresponding compound of Formula (I) where X is chloride by utilizing a suitable ion exchange resin such as Dowex 1x8–50.

Detailed descriptions of the conversion of a compound of Formula (Ia) to a compound of Formula (I) where E is —NHC(O)NH— is given in Examples 1–3.

Utility, Testing and Administration

General Utility

The compounds of the invention are CCR-3 receptor antagonists and therefore should inhibit recruitment of eosinophil, T cells, basofils and mast cells by chemokines such as RANTES, eotaxin and MCP-3. The quaternary salts of the present invention are, in general, more potent than their corresponding non-quaternized piperidine analogs. Therefore, compounds of this invention and compositions containing them are useful in the treatment of eosiniphil-induced diseases such as asthma, rhinitis, eczema, and parasitic infections in mammals, especially humans.

Testing

The CCR-3 antagonistic activity of the compounds of this invention may be measured by in vitro assays such as ligand binding and chemotaxis assays as described in more detail in Examples 5, 6 and 7. It can be assayed in vivo by Ovalbumin induced Asthma in Balb/c Mice Model as described in more detail in Example 8.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula (I) may range from approximately 0.005–20 mg per kilogram body weight of the recipient per day; preferably about 0.01–10 mg/kg/day. Thus, for administration to a 70 kg person, the dosage range would most preferably be about 0.7 mg to 0.7 g per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance.

For liposomal formulations of the drug for parenteral or oral delivery the drug and the lipids are dissolved in a suitable organic solvent e.g. tert-butanol, cyclohexane (1% ethanol). The solution is lypholized and the lipid mixture is suspended in an aqueous buffer an allowed to form a liposome. If necessary, the liposome size can be reduced by sonification. (see., Frank Szoka, Jr. and Demetrios Papahadjopoulos, "Comparative Properties and Methods of Preparation of Lipid Vesicles (Liposomes)", *Ann. Rev. Biophys. Bioeng.*, 9:467–508 (1980), and D. D. Lasic, "Novel Applications of Liposomes", *Trends in Biotech.*, 16:467–608, (1998))

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulver ized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described in Example 4.

EXAMPLES

The following preparations and examples are given to enable those skilled in the art to more clearly understand and to practice the present invention. They should not be considered as limiting the scope of the invention, but merely as being illustrative and representative thereof. Detailed descriptions of the synthesis of compounds of Formula (Ia) have been given in copending U.S. patent application Ser. No. 09/134,013, filed Aug. 14, 1998 whose disclosure is hereby incorporated by reference.

Synthetic Examples

Example 1

4-(3,4-Dichlorobenzyl)-1-ethyl-1-{3-methyl-2-[3-(3,4,5-trimethoxyphenyl)-ureido]butyl]piperidinium iodide (Table III, Cpd. 1)

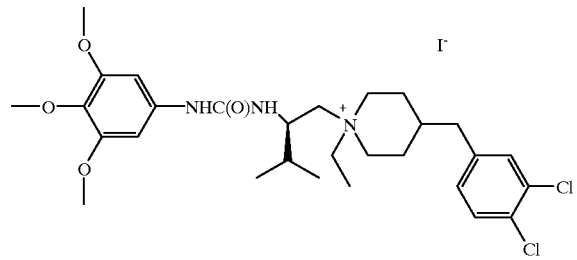

Step 1 n-Butyllithium (43.2 ml, 2 M in pentane, 108 mmol) was slowly added to an ice-cooled suspension of 3,4-dichlorobenzyl triphenylphosphonium bromide (54 g, 108 mmol) (prepared by stirring equimolar amounts of 3,4 dichlorobenzyl bromide and triphenylphosphine in THF at 65° C. overnight) in dry THF (500 ml) under an argon atmosphere. After 15 min., the reaction mixture was allowed to warm to room temperature and was stirred for an additional 2h. 1-tert-Butoxycarbonyl-4-piperidone (21.42 g, 108 mmol) was added and the stirring was continued overnight. Hexane (2 l) was added and the reaction was stirred and then filtered. The filtrate was concentrated in vacuo to give 41.8 g of an orange gum. Column chromatography on 0.5 kg flash grade silica, eluting with a gradient of 70% methylene chloride/hexane through 100% methylene chloride, followed by a gradient of 1% methanol/methylene chloride through 5% methanol/methylene chloride gave 1-(tert-butoxycarbonyl)-4-(3,4-dichloro-benzylidene)piperidine (29 g) as a light tan oil.

Step 2

Platinum oxide (0.3 g) was added to a solution of 1-(tert-butoxycarbonyl)-4-(3,4-dichlorobenzylidene)piperidine (29 g, 84.7 mmol) in ethyl acetate (500 ml) and the reaction mixture was stirred under a hydrogen atmosphere overnight. The reaction mixture was filtered through celite and the filtrate was concentrated to give 1-(tert-butoxycarbonyl)-4-(3,4-dichlorobenzyl)piperidine (30 g) as a tan oil.

Step 3

Trifluoroacetic acid (50 ml) was added to a solution of 1-(tert-butoxycarbonyl)-4-(3,4-dichlorobenzyl)piperidine (24 g, 69.7 mmol) in methylene chloride (150 ml) and the reaction mixture was stirred for 1h. The solvent was removed under reduced pressure, followed by addition of ethyl acetate (200 ml), and the resulting mixture was made basic with 1N aqueous sodium hydroxide. The organic layer was separated, dried over magnesium sulfate and the solvent was removed under reduced pressure to give 4-(3,4-dichlorobenzyl)piperidine (17.1 g) as light brown solid.

Step 4

D-BOC-Valine (1.3 g, 5.98 mmol) and 1-(3-dimethylaminopropyl)-3-ethyl-carbodiimide (1.15 g, 5.98 mmol) were added to a solution of 4-(3,4-dichloro-benzyl)piperidine (1.12 g, 4.57 mmol) in methylene chloride (15 ml) and the reaction mixture was stirred at room temperature under an argon atmosphere. After 3 h the solvents were removed under vacuo and water (10 ml) and ethyl acetate (25 ml) were added. The organic layer was separated, dried over magnesium sulfate and concentrated under reduced pressure. Column chromatography with 15–20% ethyl acetate Ihexane as the eluant gave 1-(R)-[4-(3,4-dichlorobenzyl)piperidin-1-ylcarbonyl]-N-(tert-butoxycarbonyl)-2-methylpropylamnine (1.89 g) as a gummy foam.

Step 5

To a solution of 1-(R)-[4-(3,4-dichlorobenzyl)piperidin-1-ylcarbonyl]-N-(tert-butoxycarbonyl)-2-methylpropylamine (5.9 g, 13.2 mmol) in methylene chloride (100 ml) was added trifluoroacetic acid (30 ml) at room temperature. After 4 h, the reaction mixture was concentrated and the residue was stirred with ethyl acetate (200 ml) and water (100 ml) while adjusting the pH to 8 with 15% aqueous sodium hydroxide solution. The organic layer was separated and the aqueous layer was extracted twice with ethyl acetate. The combined organic portions were dried over magnesium sulfate, filtered and concentrated in vacuo to give 1-(R)-[4-(3,4-dichlorobenzyl)piperidin-1-ylcarbonyl-2-methylpropylaamine (4.53 g) as a colorless gum.

Step 6

To a solution of 1-(R)-[4-(3,4-dichlorobenzyl)piperidin-1-ylcarbonyl-2-methyl-propylamine (4.53 g, 13.3 mmol) in dry tetrahydrofuran (100 ml) was added diborane (92.4 ml, 92.4 mmol, 1 M in THF) and the reaction mixture was stirred under argon at 65° C. After 3 h, the reaction mixture was cooled in an ice bath and aqueous hydrochloric acid (60 ml, 6 N) was slowly added with stirring. The reaction mixture was concentrated in vacuo and the aqueous solution was stirred at 100° C. After 1 h, the reaction mixture was cooled to 0° C. and potassium hydroxide pellets were slowly added until pH 8 was obtained. The solution was extracted twice with ethyl acetate (100 ml), dried over magnesium sulfate and concentrated in vacuo. The colorless liquid (3.84 g) was chromatographed, eluting with 2.5–10% MeOH/CH$_2$Cl$_2$ containing 1% NH$_4$OH. The free amine was dissolved in anhydrous ether and ethereal HCl was added to afford 1-(R)-[4-(3,4-dichlorobenzyl)piperidin-1-ylmethyl]-2-methylpropylamine as the HCl salt.

Step 7

3,4,5-Trimethoxyphenyl isocyanate (1.9 g, 9.11 mmol) was added to a solution of 1-(R)-[4-(3,4-dichlorobenzyl)piperidin-1-ylmethyl]-2-methylpropylamine (2.5 g, 7.59 mmol) in methylene chloride (25 ml) under argon atmosphere. The solution was stirred for 45 min., at room temperature, followed by 30 min., at 38° C. The reaction mixture was concentrated in vacuo. The crude product was chromatographed on a silica gel column, eluting with 1.5–2.5% MeOH/CH$_2$Cl$_2$ containing 1% NH$_4$OH to give 1-{1-(R)-[4-(3,4-dichlorobenzyl)piperidin-1-ylmethyl]-2-methylpropyl}-3-(3,4,5-trimethoxyphenyl)urea (3.7 g).

Step 8

A solution of 1-{1-(R)-[4-(3,4-dichlorobenzyl)piperidin-1-ylmethyl]-2-methylpropyl}-3-(3,4,5-trimethoxyphenyl) urea (0.19 g, 0.353 mmoles) in iodoethane (4 ml) was stirred overnight at 68° C. under argon. The yellow mixture was concentrated in vacuo and the crude product was flash chromatographed, eluting with 3%–4% methanol/methylene chloride to give 4-(3,4-dichlorobenzyl)-1-ethyl-1-{3-methyl-2-[3-(3,4,5-trimethoxyphenyl)ureidolbutyl}piperidinium iodide (0.18 g) as a yellow solid, M.Pt. 125–133° C.

Proceeding as described in Example 1 above, but substituting ethyl iodide with a solution of methyl iodide (0.5 ml) in methylene chloride (20 ml) in Step 8 and stirring the reaction mixture at room temperature overnight gave 4-(3,4-dichlorobenzyl)-1-methyl-1-{3-methyl-2-[3-(3,4,5-trimethoxyphenyl)ureido]butyl}piperidinium iodide. M.Pt. 127–248° C. (Table III, Cpd. 14)

Proceeding as described in Example 1 above, but substituting ethyl iodide with ethyl iodoacetate (5 ml) in Step 8 and stirring the reaction mixture at room temperature for 5 h gave 4-(3,4-dichlorobenzyl)-1-(ethoxycarbonylmethyl)-1-(3-methyl-2-[3-(3,4,5-trimethoxyphenyl)ureido]buty] }piperidinium iodide. M. Pt. 131–139° C. (Table III, Cpd. 17)

Proceeding as described in Example 1 above, but substituting ethyl iodide with benzyl bromide (0.5 mL in 10 mL dichloromethane at room temperature gave 4-(3,4-dichlorobenzyl)-1-benzyl-1-{3-methyl-2-[3-(3,4,5-trimethoxyphenyl)ureido]butyl}piperidinium bromide. M.P 131–207° C. (Table III, Cpd. 18)

Proceeding as described in Example 1 above, but substituting for D-Boc-Valine with Boc-glycine in step 4 and substituting ethyl iodide with a solution of methyl iodide (0.5 ml) in methylene chloride (20 ml) in Step 8 and stirring the reaction mixture at room temperature overnight gave 4-(3,4-dichlorobenzyl)-1-methyl-1-{2-[(3,4,5-trimethoxyphenyl)ureido]ethyl}piperidinium iodide. M.Pt. 102–108° C. (Table III, Cpd. 19)

Example 2

4-(3,4-Dichlorobenzyl)-1-ethyl-1-{3-methyl-2-[3-(3,4,5-trimethoxyphenyl)-ureido]butyl}piperidinium chloride (Table III, Cpd. 20)

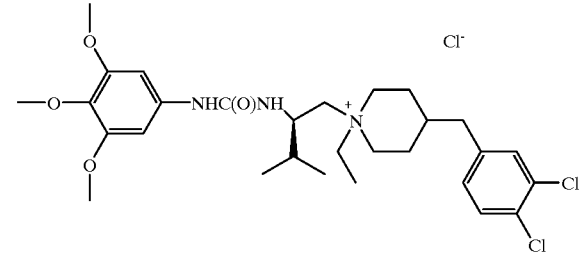

A solution of 4-(3,4-dichlorobenzyl)-1-ethyl-1-{3-methyl-2-[3-(3,4,5-trimethoxy-phenyl)ureido]butyl}piperidinium iodide (0.2 g) in methanol (5 ml) was slowly passed through a column of Dowex 1x8-50 ion exchange resin (3 g). The eluted product was concentrated in vacuo to give 4-(3,4-dichlorobenzyl)-1-ethyl-1-{3-methyl-2-[3-(3,4,5-trimethoxyphenyl)ureido]butyl}piperidinium chloride.

Proceeding as described in Example 2, but replacing 4-(3,4-dichlorobenzyl)-1-ethyl-1-{3-methyl-2-[3-(3,4,5-trimethoxy-phenyl)ureido]butyl}piperidinium iodide with 4-(3,4-dichlorobenzyl)-1-methyl-1-{3-methyl-2-[3-(3,4,5-trimethoxy-phenyl)ureido]butyl})piperidinium iodide was obtained 4-(3,4-dichlorobenzyl)-1-methyl-1-{3-methyl-2-[3-(3,4,5-trimethoxyphenyl)ureido]butyl}piperidinium chloride. M.Pt. 123.7–138° C. (Table III, Cpd. 21)

Example 3

4-(3,4-Dichlorobenzyl)-1-(2-hydroxyethyl)-1-{3-methyl-2-[3-(3,4,5-trimethoxy-phenyl)ureido]butyl}piperidinium chloride (Table III, Cpd. 16)

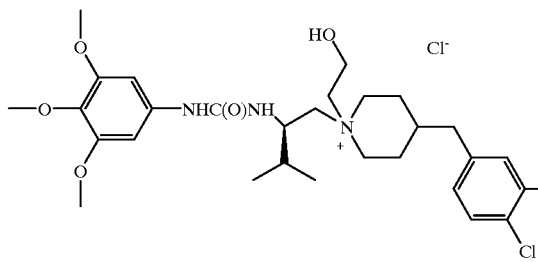

1-{1-(R)-[4-(3,4-Dichlorobenzyl)piperidin-1-ylmethyl]-2-methylpropyl}-3-(3,4,5-trimethoxyphenyl)urea (0.21 g) was dissolved in 2-chloroethanol (5 mL) and the solution heated in an oil bath at 90° C. After stirring under nitrogen for 1 day, the reaction mixture was cooled and then poured directly onto a pad of silica gel. Elution with 6% methanol in methylene chloride and then 11% methanol in methylene chloride, followed by solvent removal from the appropriate fractions gave 4-(3,4-dichlorobenzyl)-1-(2-hydroxyethyl)-1-{3-methyl-2-[3-(3,4,5-trimethoxyphenyl)ureido]butyl}piperidinium chloride (41.6 mg) as an oil.

Example 4

1-{2-(4-methylbenzoylamino)-3-methylbutyl}-4-(3,4-dichlorobenzyl)-1-methyl-piperidinium chloride (Table I, Cpd. 5)

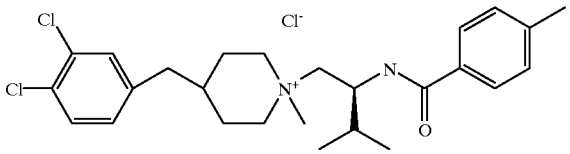

To a room temperature solution of N-{1-(S)-[4-(3,4-dichlorobenzyl)piperidin-1-ylmethyl]-2-methylpropyl}-4-methylbenzamide (0.104 g, 0.232 mmoles), prepared as described in copending patent application U.S. Ser. No. 09/134,103 filed Aug. 14, 1998, in methylene chloride (10 ml) is added iodomethane (1 ml) and stirred at room temperature overnight. The solvent was stripped and the residue was flash chromatographed on flash silica gel with a gradient of 2% through 3% methanol/methylene chloride (containing 1% ammonia). 1-{2-(4-methylbenzoylarino)-3-methylbutyl}-4-(3,4-dichlorobenzyl)-1-methyl-piperidinium iodide was obtained as a solid (12 mg). This was dissolved in methanol and passed through a glass column (25 mm i.d.) containing 2 inches of Dowex 1X8-50 ion exhange resin, previous washed with methanol. Methanol was passed through the column until no more product was detected by TLC. The solvent was stripped, affording 1-{2-(4-methylbenzoylamino)-3-methylbutyl}-4-(3,4-dichlorobenzyl)-1-methyl-piperidinium chloride (8 mg).

Example 5

4-(3,4-Dichlorobenzyl)-1-(2-carboxyethyl)-1-{3-methyl-2-[3-(3,4,5-trimethoxy-phenyl)ureido]butyl}piperidine (Table II, Cpd. 22)

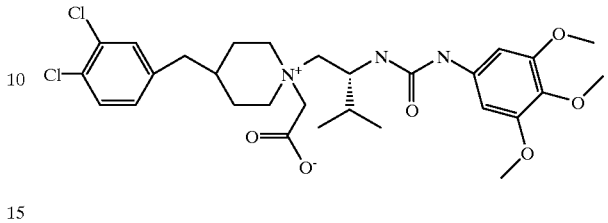

A mixture of 4-(3,4-dichlorobenzyl)-1-(2-carbethoxyethyl)-1-{3-methyl-2-[3-(3,4,5-trimethoxy-phenyl)ureido]butyl}piperidinium iodide (0.27 g, 364 mmoles, from Example 5 above), methanol (5 ml), water (5 ml), and lithium hydroxide monohydrate (30.6 mg, 0.728 mmoles) was stirred at 50 degrees for 6 hrs. After stripping the solvent, water (10 ml) and ethyl acetate (20 ml) was adding to the crude residue and the pH was adjusted to pH 7 with dilute aq. HCl. The organic layer was separated and the aqueous layer was washed with more ETOAc. The combined organic portions were dried (anhydrous magnesium sulfate) and stripped. The crude residue was chromatographed on flash silica gel with a 7% methanollmethylene chloride (containing 1% ammonia) yielding the desire product 4-(3,4-dichlorobenzyl)-1-(2-carboxyethyl)-1-{3-methyl-2-[3-(3,4,5-trimethoxy-phenyl)ureido]butyl}piperidine (90 mg) M.Pt. 180–184° C.

Example 6

Formulation Examples

The following are representative pharmaceutical formulations containing a compound of Formula (I).

Tablet Formulation
The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Capsule formulation
The following ingredients are mixed intimately and loaded into a hard-shell gelatin capsule.

| Ingredient | Quantity per tablet, mg |
| --- | --- |
| compound of this invention | 200 |
| lactose, spray-dried | 148 |
| magnesium stearate | 2 |

| Suspension formulation |  |
|---|---|
| The following ingredients are mixed to form a suspension for oral administration. | |
| Ingredient | Amount |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled Water | q.s. to 100 ml |

| Injectable formulation |  |
|---|---|
| The following ingredients are mixed to form an injectable formulation. | |
| Ingredient | Amount |
| compound of this invention | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

| Liposome formulation |  |
|---|---|
| The following ingredients are mixed to form a liposome formulation. | |
| Ingredient | Amount |
| compound of this invention | 10 mg |
| L-α-phosphatidylcholine | 150 mg |
| tert-butanol | 4 ml |

Freeze dry the sample and lyopholize overnight. Reconstitute the sample with 1 ml 0.9% saline solution. Liposome size can be reduced by sonication

| Topical formulation |  |
|---|---|
| A topical formulation is prepared with the following ingredients. | |
| Ingredient | Amount, g |
| compound of this invention | 10 |
| Span 60 | 2 |
| TWEEN ® 60 | 2 |
| inineral oil | 5 |
| petrolatum | 10 |
| methyl paraben | 0.15 |
| propyl paraben | 0.05 |
| BHA (butylated hydroxy anisole) | 0.01 |
| water | q.s. to 100 |

All of the above ingredients, except water, are combined and heated to 60–70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| compound of the invention | 500 mg |
|---|---|
| Witepsol ® H-15 | balance |

Example 7

CCR-3 Receptor Binding Assay—in vitro

The CCR-3 antagonistic activity of the compounds of the invention was determined by their ability to inhibit the binding of $^{125}$I eotaxin to CCR-3 L1.2 transfectant cells obtained from leukoSite (Cambridge, Mass.).

The assay was performed in Costar 96-well polypropylene round bottom plates. Test compounds were dissolved in DMSO and then diluted with binding buffer (50 mM HEPES, 1 mM $CaCl_2$, 5 mM $MgCl_2$, 0.5% bovine serum albumin, 0.02% sodium azide, pH 7.24) such that the final DMSO concentration was 2%. 25 μl of the test solution or only buffer with DMSO (control samples) was added to each well, followed by the addition of 25 μl of $^{125}$I-eotaxin (100 pmol) (NEX314, New England Nuclear, Boston, Mass.) and 1.5×10 of the CCR-3 L1.2 transfected cells in 25 μl binding buffer. The final reaction volume was 75 μl.

After incubating the reaction mixture for 1 h at room temperature, the reaction was terminated by filtering the reaction mixture through polyethylenimine treated Packard Unifilter GF/C filter plate (Packard, Chicago, Ill.). The filters were washed four times with ice cold wash buffer containing 10 mm HEPES and 0.5M sodium chloride (pH 7.2) and dried at 65° C. for approximately 10 min. 25 μl/well of Microscint-20™ scintillation fluid (Packard) was added and the radioactivity retained on the filters was determined by using the Packard TopCount™.

Compounds of this invention were active in this assay.

The $IC_{50}$ value (concentration of test compound required to reduce $^{125}$I-eotaxin binding to the CCR-3 L 1.2 transfected cells by 50%) for representative compounds of the invention was:

| Cpd # | $IC_{50}$, μM |
|---|---|
| 1 | 0.21 |
| 7 | 4.37 |
| 12 | 0.198 |
| 14 | 2.32 |

Example 8

Inhibition of Eotaxin Mediated Chemotaxis of CCR-3 L1.2 Transfectant Cells—In Vitro Assay The CCR-3 antagonistic activity of the compounds of this invention can be determined by measuring the inhibition of eotaxin mediated chemotaxis of the CCR-3 L1.2 transfectant cells, using a slight modification of the method described in Ponath, P. D. et al., 1996. "Cloning of the Human Eosinophil Chemoattractant, Eotaxin". *J. Clin. Invest.* 97: 604–612. The assay is performed in a 24-well chemotaxis plate (Collaborative Biomedical Products). The CCR-3 L1.2 transfectant cells, designated as 10E6, are grown in culture medium containing RPMI 1640, 10% Hyclone™ fetal calf serum, 5.5%×10 2-mercaptoethanol and G 418 (0.8 mg/ml).

18–24 hours before the assay, the transfected cells are treated with n-butyric acid at a final concentration of 5 mM/1×10⁶ cells/ml, isolated and resuspended at 1×10⁷ cells/ml in assay medium containing equal parts of RPMI 1640 and M199 with 0.5% BSA.

Human eotaxin suspended in PBS (Gibco #14190–029) at 1 mg/ml is added to bottom chamber in a final concentration of 100 nm. Biocoat™ Transwell culture inserts (Costar Corp., Cambridge Mass.) having 3 micron pore size were inserted into each well and L1.2 cells (1×10⁶) are added to the top chamber in a final volume of 100 μl. Test compounds in DMSO are added both to the top and bottom chambers such that the final DMSO volume was 0.5%. The assay is performed against two sets of controls. Positive control contained cells with no test compound in the top chamber and only eotaxin in the lower chamber. Negative control contained cells with no test compound in the top chamber and neither eotaxin nor test compound in lower chamber. The plate is incubated at 37° C. After 4 h, the inserts are removed from the chambers and the cells that have migrated to the bottom chamber are counted by pipetting out 500 μl of the cell suspension from the lower chamber to 1.2 ml Cluster tubes (Costar) and counting them on a FACS for 30 sec.

Compounds of this invention are expected to be active in this assay.

Example 9

Inhibition of Eotaxin Mediated Chemotaxis of Human Eosinophils—In Vitro Assay

The ability of compounds of the invention to inhibit eotaxin mediated chemotaxis of human eosinophils can be assessed using a slight modification of procedure described in Carr, M. W. et al., *Proc. Natl. Acad. Sci. USA*, 91: 3652–3656 (1994). Experiments are performed using 24 well chemotaxis plates (Collaborative Biomedical Products). Eosinophils are isolated from blood using the procedure described in PCT Application, Publication No. WO 96/22371. The endothelial cells that should be used are the endothelial cell line ECV 304 that can be obtained from European Collection of Animal Cell Cultures (Porton Down, Salisbury, U.K.). Endothelial cells are cultured on 6.5 mm diameter Biocoat® Transwell tissue culture inserts (Costar Corp., Cambridge Mass.) with a 3.0 μM pore size. Culture media for ECV 304 cells consists of M199, 10% Fetal Calf Serum, L-glutamine and antibiotics. Assay media consists of equal parts RPMI 1640 and M199, with 0.5% BSA. 24 h before the assay 2×10⁵ ECV 304 cells are plated on each insert of the 24-well chemotaxis plate and incubated at 37° C. 20 nM of eotaxin diluted in assay medium is added to the bottom chamber. The final volume in bottom chamber was 600 μl. The endothelial coated tissue culture inserts are inserted into each well. 10⁶ eosinophil cells suspended in 100 μl assay buffer are added to the top chamber. Test compounds dissolved in DMSO are added to both top and bottom chambers such that the final DMSO volume in each well is 0.5%. The assay is performed against two sets of controls. Positive control contains cells in the top chamber and eotaxin in the lower chamber. Negative control contains cells in the top chamber and only assay buffer in the lower chamber. The plates are incubated at 37° C. in 5% $CO_2$/95% air for 1–1.5 h.

The cells that have migrated to the bottom chamber are counted using flow cytometry. 500 μl of the cell suspension from the lower chamber is placed in a tube, and relative cell counts is obtained by acquiring events for a set time period of 30 seconds.

Compounds of this invention are expected to be active in this assay.

Example 10

Inhibition of Eosinophil Chemotaxis by CCR-3 Antagonist in Ovalbumin Sensitized balb/c mice— In Vivo Assay The CCR-3 antagonistic activity of the compounds of the invention can be determined by measuring the inhibition of eosinophil accumulation into the BAL fluid of Ovalbumin (OA)-sensitized balbic mice after antigen challenge by aerosol. Briefly, male balb/c mice weighing 20–25 g are sensitized with OA (10 μg in 0.2 ml aluminum hydroxide solution) intraperitoneally on days 1 and 14. After a week, the mice are divided into ten groups. Test compounds or vehicle (positive control group) are administered. After 1 h, the mice are placed in a Plexiglass box and exposed to OA aerosol generated by a PARISTAR™ nebulizer for 20 min. Mice which have not been sensitized or challenged are included as negative control. After 24 or 72 h, the mice are anesthetized (urethane, approx. 1 g/kg, i.p.), a tracheal cannula (PE 60 tubing) is inserted and the lungs are lavaged four times with 0.3 ml PBS. The Bal fluid is transferred into plastic tubes and kept on ice. Total leukocytes in a 20 μl aliquot of the BAL fluid is determined by hemocytometer and/or Coulter Counter™. Differential leukocyte counts are made on Cytospin preparations which have been stained with a modified Wright's stain (Diff-Quick™) by light microscopy using standard morphological criteria.

Compounds of this invention are expected to be active in this assay.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound selected from compounds of Formula (I):

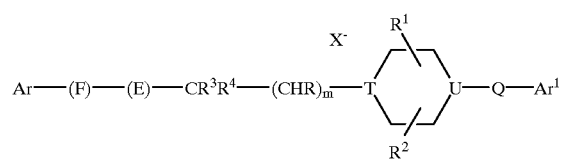

(I)

wherein:

One of T and U is —N⁺R⁵— where R⁵ is alkyl, haloalkyl, cyanoalkyl, hydroxyalkyl, alkoxyalkyl, carboxyalkyl, alkoxycarbonylalkyl, amidoalkyl, sulfonylaminoalkyl, or aralkyl and the other is —CH—;

X⁻ is a pharmaceutically acceptable counterion;

$R^1$ and $R^2$ are, independently of each other, hydrogen or alkyl;

m is an integer from 0 to 3 provided that when T is $-N^+R^5-$ then m is at least 1;

Ar and $Ar^1$ are, independently of each other, aryl or heteroaryl;

F is alkylene, alkenylene or a bond;

R is hydrogen or alkyl; or R together with either $R^3$ or $R^4$ and the atoms to which they are attached forms a carbocycle or a heterocycle;

$R^3$ and $R^4$ are, independently of each other, hydrogen, alkyl, alkenyl, haloalkyl, cycloalkyl, cycloalkylalkyl, aryl, aralkyl, heteroaryl, heteroaralkyl, heterocyclyl, heterocyclylalkyl, or -(alkylene)-C(O)—Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy; with the proviso that $R^3$ and $R^4$ are not both H;

E is $-C(O)N(R^6)-$, $-SO_2N(R^6)-$, $-N(R^7)C(O)N(R^6)-$, $-N(R^7)SO_2N(R^6)-$, $-N(R^7)C(S)N(R^6)-$, $-N(R^7)C(O)-$ or $-N(R^7)SO_2-$ where:

$R^6$ and $R^7$ are, independently of each other, hydrogen, alkyl, acyl, haloalkyl, cycloalkyl, cycloalkylalkyl, aryl, aralkyl, aralkenyl, heteroaryl, heteroaralkyl, heterocycloalkyl, or -(alkylene)-C(O)—Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy;

Q is —CO— or an alkylene chain optionally interrupted by $-C(O)-$, $-NR^8-$, $-O-$, $-S(O)_{0-2}-$, $-C(O)N(R^8)-$, $-N(R^8)C(O)-$, $-N(R^8)SO_2$, $-SO_2N(R^8)$, $-N(R^9)C(O)N(R^{10})-$, $-N(R^9)SO_2N(R^{10})-$ or $-N(R^9)C(S)N(R^{10})-$ where:

$R^8$, $R^9$ and $R^{10}$ are, independently of each other, hydrogen, alkyl, acyl, haloalkyl, cycloalkyl, cycloalkylalkyl, aryl, aralkyl, aralkenyl, heteroaryl, heteroaralkyl, heterocyclylalkyl, or -(alkylene)-C(O)—Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy;

wherein aryl is a monovalent monocyclic or bicyclic aromatic hydrocarbon radical of 6 to 10 ring atoms, optionally substituted independently with one, two or three alkyl, haloalkyl, cycloalkyl, cycloalkylalkyl, halo, cyano, nitro, acyloxy, phenyl, heteroaryl, heteroaralkyl, amino, monosubstituted amino, disubstituted amino, acylamino, hydroxylamino, amidino, guanidino, cyanoguanidinyl, hydrazino, hydrazido, $-OR^{11}$ wherein $R^{11}$ is hydrogen, alkyl, haloalkyl, alkenyl, cycloalkyl, cycloalkylalkyl, phenyl, heteroaralkyl or heteroaryl; $-S(O)_nR^{12}$ wherein n is an integer from 0 to 2 and $R^{12}$ is hydrogen, alkyl, haloalkyl, cycloalkyl, cycloalkylalkyl, phenyl, heteroaryl, heteroaralkyl, amino, mono- or disubstituted amino, $-NR^{13}SO_2R'$ wherein $R^{13}$ is hydrogen or alkyl and R' is alkyl, amino, mono- or disubstituted amino; $-C(O)R^{14}$ wherein $R^{14}$ is hydrogen, alkyl, cycloalkyl, cycloalkylalkyl, haloalkyl or phenyl; $-COOR^{15}$ wherein $R^{15}$ is hydrogen, alkyl, phenyl, heteroaryl or heteroaralkyl; -(alkylene)$COOR^{15}$; methylenedioxy, 1,2-ethylenedioxy, $-CONR^{16}R^{17}$ or -(alkylene)$CONR^{16}R^{17}$ wherein $R^{16}$ and $R^{17}$ are independently selected from hydrogen, alkyl, cycloalkyl, haloalkyl, cycloalkylalkyl, phenyl, heteroaryl and heteroaralkyl;

wherein heteroaryl is a monovalent monocyclic or bicyclic aromatic radical of 5 to 10 ring atoms containing one, two, or three ring heteroatoms selected from N, O, or S, the remaining ring atoms being C, optionally substituted independently with one or two alkyl, haloalkyl, cycloalkyl, cycloalkylalkyl, halo, cyano, nitro, acyloxy, phenyl, amino, mono- or disubstituted amino, acylamino, hydroxyamino, amidino, guanidino, cyanoguanidinyl, hydrazino, hydrazido, $-OR^{18}$ wherein $R^{18}$ is hydrogen, alkyl, haloalkyl, cycloalkyl, cycloalkylalkyl or phenyl, $-S(O)_nR^{19}$ wherein n is an integer from 0 to 2 and $R^{19}$ is hydrogen, alkyl, haloalkyl, cycloalkyl, cycloalkylalkyl, phenyl, amino, mono- or disubstituted amino; $-C(O)R^{14}$, $-COOR^{20}$ wherein $R^{20}$ is hydrogen, alkyl, or phenyl; -(alkylene)$COOR^{21}$ wherein $R^{21}$ is hydrogen, alkyl or phenyl; methylenedioxy, 1,2-ethylenedioxy, $-CONR^{22}R^{23}$ or -(alkylene)$-CONR^{22}R^{23}$ wherein $R^{22}$ and $R^{23}$ are independently hydrogen, alkyl, cycloalkyl, haloalkyl, cycloalkylalkyl or phenyl;

wherein heterocycle is a saturated or unsaturated cyclic radical of 3 to 8 ring atoms in which one or two ring atoms are heteroatoms selected from N, O, or $S(O)_n$, wherein n is an integer from 0 to 2, optionally substituted independently with one, two or three alkyl, haloalkyl, cycloalkyl, cycloalkylalkyl, aryl, aralkyl, heteroaryl, heteroaralkyl, halo, cyano, acyl, acylamino, amino, monosubstituted amino, disubstituted amino, $-COOR^{13}$, $-XR^{24}$ wherein X is O or $S(O)_n$, wherein n is an integer from 0 to 2 and $R^{24}$ is hydrogen, alkyl, haloalkyl, cycloalkyl, aralkyl, aryl, heteroaryl or heteroaralkyl; or $-CON(R^{13})_2$;

wherein the phenyl substituent is optionally substituted independently with one, two or three substituents selected from alkyl, haloalkyl, halo, nitro, cyano, $-OR^{13}$, $N(R^{13})_2$ wherein each $R^{13}$ is hydrogen or alky, $-COOR^{13}$ or $-CON(R^{13})_2$;

wherein when (a) aryl or heteroaryl are substituted with alkyl, cycloalkyl or cycloalkylalkyl or (b) $R^3$, $R^4$, $R^6$, $R^7$, $R^8$, $R^9$, $R^{10}$ or $R^{14}$ are alkyl, cycloalkyl or cycloalkylalkyl; alkyl, cycloalkyl or cycloalkylalkyl are optionally substituted with $R^{25}$, which is $-NR^aR^b$, $-OR^a$ or $-S(O)_nR^c$, wherein n is an integer from 0 to 2, $R^a$ is hydrogen, alkyl, haloalkyl, cycloalkyl or cycloalkylalkyl, phenyl, pyridyl, $-COR^d$, wherein $R^d$ is alkyl or alkoxy or is aminoalkyl; $R^b$ is hydrogen, alkyl, $-SO_2R^e$, wherein $R^e$ is alkyl or hydroxyalkyl; $-SO_2(R^{13})_2$, or $-CON(R^{13})_2$; and $R^c$ is hydrogen, alkyl, cycloalkyl or cycloalkylalkyl, phenyl, amino or mono- or disubstituted amino; and individual isomers, mixtures of isomers, and pharmaceutically acceptable salts thereof.

2. The compound of claim 1, wherein:

T is $-N^+R^5-$ where $R^5$ is alkyl;

F is a bond; and

R, $R^1$, $R^2$, and $R^3$ are hydrogen.

3. The compound of claim 2, wherein:

m is 1;

$R^5$ is methyl or ethyl; and

Q is a methylene chain.

4. The compound of claim 3, wherein E is $-C(O)N(R^6)-$, $-SO_2N(R^6)-$, $-N(R^7)C(O)N(R^6)-$ or $-N(R^7)C(O)-$ where $R^6$ and $R^7$ are hydrogen.

5. The compound of claim 4, wherein E is $-C(O)NH-$; and $R^4$ is alkyl, optionally substituted with $R^{25}$.

6. The compound of claim 5, wherein Ar and $Ar^1$ are aryl rings.

7. The compound of claim 6, wherein

Ar is a phenyl ring optionally substituted with one, two or three substituents selected from alkyl, alkoxy, C(O) alkyl, $SO_2R^{12}$, wherein $R^{12}$ is alkyl, amino or mono or disubstituted amino; methylenedioxy, hydroxy, halo, acylamino, amino, mono- or disubstituted amino, —$CONR^{16}R^{17}$, -(alkylene)—$CONR^{16}R^{17}$, wherein $R^{16}$ and $R^{17}$ are hydrogen or alkyl, $COOR^{15}$, -(alkylene)$COOR^{15}$ wherein $R^{15}$ is hydrogen on alkyl, or $NR^{13}SO_2R'$ wherein $R^{13}$ is hydrogen or alkyl and R' is alkyl, amino, mono- or disubstituted amino); and $Ar^1$ is a phenyl ring optionally substituted with one, two or three substituent selected from alkyl, cycloalkyl or cycloalkylalkyl, each optionally substituted with —$R^{25}$, alkoxy, halo, trifluoromethyl, nitro, or mono- or disubstituted amino.

8. The compound of claim 7, wherein:

$R^4$ is 1-methylethyl, 1,1-dimethylethyl, 2-methylpropyl, 3-hydroxypropyl, 1-hydroxyethyl or 2-hydroxyethyl; and $Ar^1$ is 4-nitrophenyl, 4-trifluoromethylphenyl, 4-chlorophenyl, 3,4-difluorophenyl, 2,3-dichlorophenyl, 3-methyl-4-nitrophenyl, 3-chloro-4-fluoro-phenyl or 3,4-dichlorophenyl.

9. The compound of claim 8, wherein:

Ar is phenyl, 4-chlorophenyl, 3,4-difluorophenyl, 4-methylphenyl, 4-methoxyphenyl, 4-hydroxyphenyl, 4-dimethylaminophenyl, 4-aminocarbonyl-phenyl, 4-acetylphenyl, 4-acetylaminophenyl, 4-dimethylaminocarbonylphenyl, 3,4-methylenedioxyphenyl, 4-methylsulfonylphenyl, 4-[(2-acetylamino)ethyl]-phenyl, 4-{2-[(R)-amino-3-methylbutyrylarnino]ethyl}phenyl, 4(2-aminoethyl)-phenyl, 4-(aminomethyl)-phenyl, 4-(hydroxymethyl) phenyl, 2,5-dimethoxyphenyl, 3,5-dimethoxyphenyl, 3,4-dimethoxyphenyl, 3,4,5-trimethoxyphenyl, 4-amino-carbonylmethylphenyl, 4-acetylaminomethylphenyl, 4-methylsulfonylaminophenyl, 4-methylsulfonylaminomethylphenyl or 4-aminophenyl.

10. The compound of claim 4, wherein E is —NHC(O)NH—; and $R^4$ is alkyl, optionally substituted with $R^{25}$.

11. The compound of claim 10, wherein Ar and $Ar^1$ are optionally substituted aryl rings.

12. The compound of claim 11, wherein:

Ar is a phenyl ring optionally substituted with one, two or three substituents selected from alkyl, alkoxy, C(O)(alkyl), $SO_2R^{12}$ wherein $R^{12}$ is alkyl, amino or mono or disubstituted amino; methylenedioxy, hydroxy, halo, acylamino, amino, mono- or disubstituted amino, C(O)$NR^{16}R^{17}$, -(alkylene)-C(O)$NR^{16}R^{17}$, wherein $R^{16}$ and $R^{17}$ are hydrogen or alkyl, $COOR^{15}$ or -(alkylene]$COOR^{15}$ wherein $R^{15}$ is hydrogen or alkyl or $NR^{13}SO_2R'$, wherein $R^{13}$ is hydrogen or alkyl and R' is alkyl, amino, mono- or disubstituted amino; and $Ar^1$ is a phenyl ring optionally substituted with one, two or three substituent selected from alkyl, cycloalkyl, or cycloalkylalkyl, each optionally substituted with $R^{25}$, alkoxy, halo, trifluoromethyl, nitro, or mono- or disubstituted amino.

13. The compound of claim 12, wherein:

$R^4$ is 1-methylethyl, 1,1-dimethylethyl, 2-methylpropyl, 3-hydroxypropyl, 1-hydroxyethyl or 2-hydroxyethyl; and $Ar^1$ is 4-nitrophenyl, 4-trifluoromethylphenyl, 4-chlorophenyl, 3,4-difluorophenyl, 2,3-dichlorophenyl, 3-methyl-4-nitrophenyl, 3-chloro-4-fluorophenyl or 3,4-dichlorophenyl.

14. The compound of claim 13, wherein:

Ar is phenyl, 3-methoxyphenyl, 3-methylsulfonylphenyl, 3-dimethyl—aminophenyl, 3-acetylaminophenyl, 3-acetylphenyl, 3-dimethylaminocarbonyl-phenyl, 3-[(2-acetylamino)ethyl]-phenyl, 3-aminocarbonylphenyl, 3-carboxyphenyl, 2,5-dimethoxyphenyl, 3,5-dimethoxy-phenyl, 3,4-dimethoxy-phenyl, 3,4,5-trimethoxyphenyl, 3-aminocarbonylmethylphenyl, 3-acetylamino-methylphenyl, 3-carboxymethylphenyl, 3-methylsulfonylaminophenyl, 3-methylsulfonylaminomethylphenyl, or 3-aminophenyl.

15. The compound of claim 14 wherein:

$Ar^1$ is 3,4,5-trimethoxyphenyl;

$Ar^2$ is 3,4-dichlorophenyl;

$R^4$ is 1-methylethyl;

$R^5$ is methyl;

$X^-$ is iodide, namely 4-(3,4-dichlorobenzyl)-1-methyl-1-{3-methyl-2-(R)-[3-(3,4,5-trimethoxyphenyl)ureido]butyl}piperidinium iodide.

16. The compound of claim 1, wherein:

T is —$N^+R^5$— where $R^5$ is hydroxyalkyl;

F is a bond; and

R, $R^1$, $R^2$, and $R^3$ are hydrogen.

17. The compound of claim 16, wherein:

m is 1;

$R^5$ is methyl or ethyl; and

Q is a methylene chain.

18. The compound of claim 1, wherein:

T is —$N^+R^5$— where $R^5$ is alkoxycarbonylalkyl;

F is a bond; and

R, $R^1$, $R^2$, and $R^3$ are hydrogen.

19. The compound of claim 18, wherein:

m is 1;

$R^5$ is methyl or ethyl; and

Q is a methylene chain.

20. A pharmaceutical composition comprising a therapeutically effective amount of a compound of claim 1 and a pharmaceutically acceptable excipient.

21. A method of treatment of a disease in a mammal treatable by administration of a CCR-3 antagonist, comprising administration to the mammal of a therapeutically effective amount of a compound of claim 1.

22. The method of claim 21, wherein the disease is asthma.

23. A process for preparing a compound of claim 1, which comprises:

(1) reacting a compound of Formula (Ia)

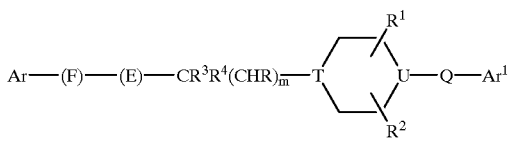

(Ia)

where T or U is nitrogen, R, $R^1$, $R^2$, $R^3$, $R^4$, Ar, $Ar^1$, E, F and Q are as defined in claim 1, with an alkylating agent of formula $R^5X$ where $R^5$ is as defined in claim 1 and X is a leaving group under alkylating conditions;

(2) optionally replacing one counterion in the compound of Formula (I) prepared in Step (1) with another counterion; and (3) optionally converting the compound of Formula (I) prepared in Steps (1) or (2) above, to the corresponding acid addition salt by treatment with an acid.

* * * * *